US012283041B2

(12) United States Patent
Park et al.

(10) Patent No.: US 12,283,041 B2
(45) Date of Patent: Apr. 22, 2025

(54) USER INTERFACE FOR VIDEO ANALYSIS

(71) Applicant: VUNO Inc., Seoul (KR)

(72) Inventors: Hyunho Park, Seoul (KR);
Gwangbeen Park, Seoul (KR);
Seungho Lee, Seoul (KR)

(73) Assignee: VUNO Inc., Seoul (KR)

(*) Notice: Subject to any disclaimer, the term of this patent is extended or adjusted under 35 U.S.C. 154(b) by 544 days.

(21) Appl. No.: 17/501,491

(22) Filed: Oct. 14, 2021

(65) Prior Publication Data
US 2022/0122249 A1    Apr. 21, 2022

(30) Foreign Application Priority Data

Oct. 15, 2020  (KR) .................. 10-2020-0133098
Feb. 10, 2021  (KR) .................. 10-2021-0019002

(51) Int. Cl.
*G06T 7/00*    (2017.01)
*G06F 3/0482*  (2013.01)
(Continued)

(52) U.S. Cl.
CPC .......... *G06T 7/0012* (2013.01); *G06F 3/0482* (2013.01); *G06T 7/0014* (2013.01);
(Continued)

(58) Field of Classification Search
CPC ....... G06T 7/0012; G06T 7/0014; G06T 7/11; G06T 7/62; G06T 2200/24;
(Continued)

(56) References Cited

U.S. PATENT DOCUMENTS 10,699,410 B2    6/2020  Pheiffer et al.
2006/0025670 A1*  2/2006  Kim .................. G16H 80/00
                                                    600/407
(Continued)

FOREIGN PATENT DOCUMENTS

JP    2014-127011 A    7/2014
JP    6382921 B2    8/2018
(Continued)

OTHER PUBLICATIONS

Robb, R.A. and Barillot, C., 1989. Interactive display and analysis of 3-D medical images. IEEE transactions on medical imaging, 8(3), pp. 217-226.*

*Primary Examiner* — Zhitong Chen
(74) *Attorney, Agent, or Firm* — Seed IP Group LLP

(57) ABSTRACT

An embodiment of the present disclosure provides a method of providing a User Interface for serial images analysis in a user equipment, the method including: displaying a first cross-sectional image, a second cross-sectional image, and a third cross-sectional image on a first area of the user interface, which are related to a first image; displaying candidate nodule information related to the first image on at least one of the first cross-sectional image, the second cross-sectional image, and the third cross-sectional image; determining the candidate nodule information related to a user input as first nodule information related to the first image, based on the user input on the user interface; and displaying the first nodule information in such a way that the candidate nodule information related to the user input is replaced with the first nodule information, in which the candidate nodule information may be generated based on a first nodule dataset obtained by inputting the first image to a deep learning algorithm in a server.

20 Claims, 13 Drawing Sheets

(51) Int. Cl.
*G06T 7/11* (2017.01)
*G06T 7/62* (2017.01)
*G06V 20/40* (2022.01)
*G16H 15/00* (2018.01)
*G16H 30/40* (2018.01)
*G16H 50/20* (2018.01)
*G16H 50/70* (2018.01)

(52) U.S. Cl.
CPC .................. *G06T 7/11* (2017.01); *G06T 7/62* (2017.01); *G06V 20/46* (2022.01); *G16H 15/00* (2018.01); *G16H 30/40* (2018.01); *G16H 50/20* (2018.01); *G16H 50/70* (2018.01); *G06T 2200/24* (2013.01); *G06T 2207/10016* (2013.01); *G06T 2207/20081* (2013.01); *G06T 2207/30064* (2013.01); *G06V 2201/032* (2022.01)

(58) Field of Classification Search
CPC . G06T 2207/10016; G06T 2207/20081; G06T 2207/30064; G06F 3/0482; G06V 20/46; G06V 2201/032; G06V 10/44; G06V 10/759; G06V 10/82; G06V 10/25; G16H 15/00; G16H 30/40; G16H 50/20; G16H 50/70; G16H 40/67
See application file for complete search history.

(56) References Cited

U.S. PATENT DOCUMENTS

| | | | |
|---|---|---|---|
| 2013/0085778 A1* | 4/2013 | Guertin | G06F 3/0482 |
| | | | 705/3 |
| 2014/0193051 A1 | 7/2014 | Lee et al. | |
| 2018/0004806 A1 | 1/2018 | Ohashi et al. | |
| 2018/0160996 A1 | 6/2018 | Lee et al. | |
| 2020/0225811 A1 | 7/2020 | Sieniek | |
| 2022/0068449 A1* | 3/2022 | Klassen | G06F 40/40 |
| 2022/0172809 A9* | 6/2022 | Lyman | G16H 40/67 |

FOREIGN PATENT DOCUMENTS

| | | |
|---|---|---|
| KR | 10-2014-0091176 A | 7/2014 |
| KR | 10-1923183 B1 | 11/2018 |
| KR | 10-2001790 B1 | 7/2019 |
| KR | 10-2020-0004204 A | 1/2020 |
| KR | 10-2020-0106326 A | 9/2020 |
| WO | 2019/190518 A1 | 10/2019 |

* cited by examiner

Fig.4

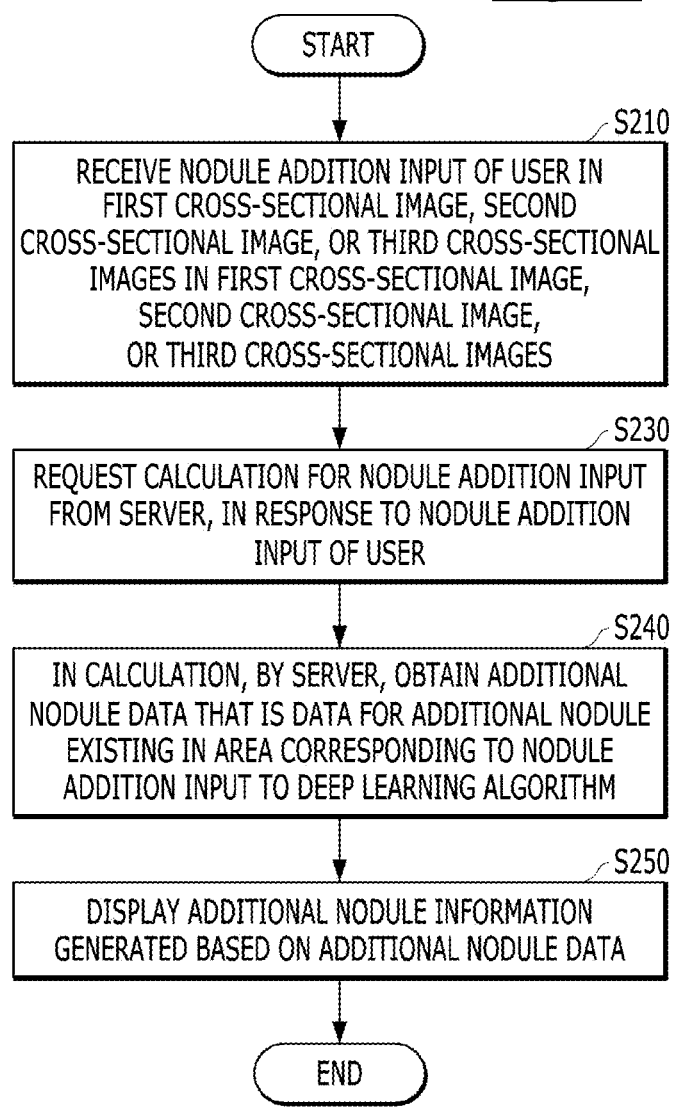

USER INTERFACE FOR VIDEO ANALYSIS

CROSS-REFERENCE TO RELATED APPLICATIONS

This application claims priority to and the benefit of Korean Patent Application No. 10-2020-0133098 filed in the Korean Intellectual Property Office on Oct. 15, 2020, and Korean Patent Application No. 10-2021-0019002 filed in the Korean Intellectual Property Office on Feb. 10, 2021, the entire contents of which are incorporated herein by reference.

BACKGROUND

Technical Field

The present disclosure relates to a serial images analysis technology, and particularly, to a user interface for analyzing a medical image, such as a lung C image.

Description of the Related Art

Medical images, especially medical images of X-rays, Computed Tomography (CT), Magnetic Resonance Imaging (MRI), and Ultra Sound, may observe abnormalities in the body, for example, lungs, bronchial tubes, and heart, so that such medical images are frequently used for reading.

Some observations that can be read through medical images are not easy to read so that even a radiologist can barely distinguish the corresponding features and shapes only through many years of training, so the some observations may be easily overlooked by a human doctor. Particularly, when it becomes more difficult reading an image, such as a nodule, the more likely it is that doctors may overlook the nodule even if the doctor pays close attention, which may cause a problem.

In order to assist the reading of the images that can be easily overlooked by humans, the need for Computer-Aided Diagnosis (CAD) has emerged, and the existing CAD technology only assists doctors in making decisions in a very limited area.

For example, Korean Patent Application Laid-Open No. 10-2014-0091176 discloses a device and a method of assisting a diagnosis of lesions. However, the prior art literature does not specifically disclose the process or statistical or computational steps in which a determination model (or "judging model" as a word mixed with the determination model in the prior art literature) that determines an area around a lesion is performed, so that there is a problem in that those skilled in the art cannot implement the technology by reading the content of the disclosure.

BRIEF SUMMARY

Accordingly, the present disclosure has been made in an effort to provide a user interface for serial images analysis.

The technical benefits of the present disclosure are not limited to the foregoing technical benefits, and other non-mentioned technical benefits will be clearly understood by those skilled in the art from the description below.

An embodiment of the present disclosure provides a method of providing a User Interface (UI) for serial images analysis in a user equipment, the method including:

displaying a first cross-sectional image, a second cross-sectional image, and a third cross-sectional image on a first area of the user interface, which are related to a first image; displaying candidate nodule information related to the first image on at least one of the first cross-sectional image, the second cross-sectional image, and the third cross-sectional image; determining the candidate nodule information related to a user input as first nodule information related to the first image, based on the user input on the user interface; and displaying the first nodule information in such a way that the candidate nodule information related to the user input is replaced with the first nodule information, in which the candidate nodule information may be generated based on a first nodule dataset obtained by inputting the first image to a deep learning algorithm in a server.

The determining of the candidate nodule information related to the user input as the first nodule information related to the first image may include: when the user input is a change input, changing the candidate nodule information based on the change input, and determining the changed candidate nodule information as the first nodule information; and when the change input is not received or the user input is a confirmation input, determining the candidate nodule information as the first nodule information.

The method may further include displaying first nodule detailed information which is generated to be associated with the candidate nodule information or the first nodule information based on the first nodule dataset, on a second area of the user interface, in which the second area on which the first nodule detailed information is displayed is capable of receiving the user input.

The method may further include generating a second nodule dataset by reflecting the first nodule information or the first nodule detailed information to the first nodule dataset, in which the generated second nodule dataset is capable of being transmitted to the server.

The one or more nodule data may include at least one of an identification data for the nodule, a location data for the nodule, a segmentation data for the nodule, diameter data for the nodule, a volume data for the nodule, a classification data for the nodule, a Lung-RADS score data for the nodule, or a malignancy risk data for the nodule.

The displaying of the candidate nodule information related to the first image on at least one of the first cross-sectional image, the second cross-sectional image, and the third cross-sectional image may include displaying the candidate nodule information on a cross-sectional image having the largest diameter of the nodule among the first cross-sectional image, the second cross-sectional image, or the third cross-sectional image, based at least on the diameter data.

The method may further include: receiving an additional nodule data for an additional nodule existing in an area corresponding to a nodule addition input, in response to the nodule addition input of a user in the first cross-sectional image, the second cross-sectional image, or the third cross-sectional image; and displaying additional nodule information generated based on the additional nodule data.

The method may further include: requesting an operation for a nodule addition input to the server, in response to the nodule addition input of a user in the first cross-sectional image, the second cross-sectional image, or the third cross-sectional image; and receiving an additional nodule data obtained by the operation from the server, and displaying additional nodule information generated based on the received additional nodule data, in which the operation may be to obtain the additional nodule data, which is data for an additional nodule existing in an area corresponding to the nodule addition input, by inputting the area corresponding to the nodule addition input to the deep learning algorithm, in the server.

The displaying of the additional nodule information generated based on the received additional nodule data may include additionally displaying the additional nodule information generated based on the additional nodule data on at least one of the first cross-sectional image, the second cross-sectional image, or the third cross-sectional image, and displaying additional nodule detailed information generated to be associated with the additional nodule information based on the additional nodule data, on the second area of the user interface.

The method may further include displaying an image list including the first image on a third area of the user interface.

The method may further include displaying a list of a related image related to the first image on a fourth area of the user interface, in response to a selection input for the first image, in which the related image may be an image taken for the same subject as the subject of the first image, at a time before taking the first image.

The method may further include: displaying a first cross-sectional image for comparison related to the first image and a second cross-sectional image for comparison related to the second image on the first area, in response to the comparison selection input of a user for the second image among the related images.

The first cross-sectional image for comparison and the second cross-sectional image for comparison may be displayed by interworking.

The method may further include: additionally displaying second nodule information generated based on a third nodule dataset on the first cross-sectional image for comparison, in which the third nodule dataset may be obtained by matching the first image and the second image through the deep learning algorithm, in order to identify a change of a nodule present in the first image, and the second nodule information may be generated based on the third nodule dataset updated by reflecting the determined first nodule information.

The method may further include additionally displaying second nodule detailed information generated to be associated with the second nodule information based on the updated third nodule dataset, on the second area, in which the second nodule detailed information may be visually distinguished from the first nodule detailed information.

The method may further include: receiving a report request input for the first image; when the second nodule information does not exist, generating a report based on the first nodule information; and when the second nodule information exists, generating a report based on the second nodule information.

The technical solutions obtainable from the present disclosure are not limited to the foregoing solutions, and other non-mentioned solution means will be clearly understood by those skilled in the art from the description below.

According to several embodiments of the present disclosure, it is possible to provide a user interface for serial images analysis.

The effects of the present disclosure are not limited to the foregoing effects, and other non-mentioned effects will be clearly understood by those skilled in the art from the description below.

BRIEF DESCRIPTION OF THE SEVERAL VIEWS OF THE DRAWINGS

Various aspects are described with reference to the drawings, and herein, like reference numerals are generally used to designate like constituent elements. In the embodiment below, for the purpose of description, a plurality of specific and detailed matters is suggested in order to provide general understanding of one or more aspects. However, it is apparent that the aspect(s) may be carried out without the specific and detailed matters.

FIG. 4 is a diagram illustrating an example of a user interface for generating an image list according to several embodiments of the present disclosure.

FIG. 9B is a flowchart for processing a nodule additional input according to several embodiments of the present disclosure.

DETAILED DESCRIPTION

Figure 1:
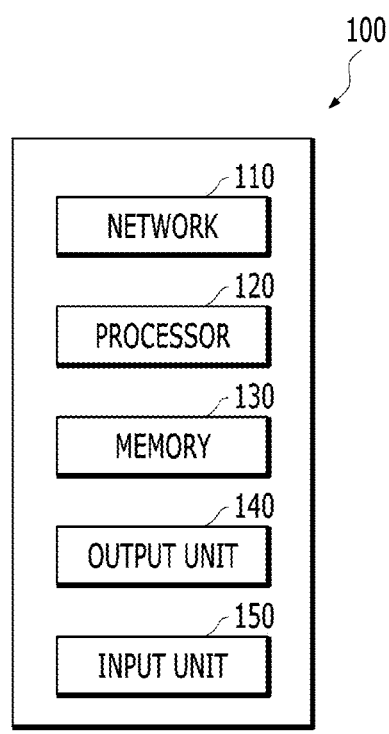
FIG. 1 is a block diagram illustrating a computing device for providing a user interface for serial images analysis according to several embodiments of the present disclosure.

Various embodiments are described with reference to the drawings. In the present specification, various descriptions are presented for understanding the present disclosure. However, it is obvious that the embodiments may be carried out even without a particular description.

Terms, "component," "module," "system," and the like used in the present specification indicate a computer-related entity, hardware, firmware, software, a combination of software and hardware, or execution of software. For example, a component may be a procedure executed in a processor, a processor, an object, an execution thread, a program, and/or a computer, but is not limited thereto. For example, both an application executed in a computing device and a computing device may be components. One or more components may reside within a processor and/or an execution thread. One component may be localized within one computer. One component may be distributed between two or more computers. Further, the components may be executed by various computer readable media having various data structures stored therein. For example, components may communicate through local and/or remote processing according to a signal (for example, data transmitted to another system through a network, such as the Internet, through data and/or a signal from one component interacting with another component in a local system and a distributed system) having one or more data packets.

A term "or" intends to mean comprehensive "or" not exclusive "or." That is, unless otherwise specified or when it is unclear in context, "X uses A or B" intends to mean one of the natural comprehensive substitutions. That is, when X uses A, X uses B, or X uses both A and B, "X uses A or B" may be applied to any one among the cases. Further, a term "and/or" used in the present specification shall be understood to designate and include all of the possible combinations of one or more items among the listed relevant items.

It should be understood that a term "include" and/or "including" means that a corresponding characteristic and/or a constituent element exists. Further, a term "include" and/or "including" means that a corresponding characteristic and/or a constituent element exists, but it shall be understood that the existence or an addition of one or more other characteristics, constituent elements, and/or a group thereof is not excluded. Further, unless otherwise specified or when it is unclear in context that a single form is indicated in context, the singular shall be construed to generally mean "one or more" in the present specification and the claims.

The term "at least one of A and B" should be interpreted to mean "the case including only A," "the case including only B," and "the case where A and B are combined."

Those skilled in the art shall recognize that the various illustrative logical blocks, configurations, modules, circuits, means, logic, and algorithm operations described in relation to the embodiments additionally disclosed herein may be implemented by electronic hardware, computer software, or in a combination of electronic hardware and computer software. In order to clearly exemplify interchangeability of hardware and software, the various illustrative components, blocks, configurations, means, logic, modules, circuits, and operations have been generally described above in the functional aspects thereof. Whether the functionality is implemented as hardware or software depends on a specific application or design restraints given to the general system. Those skilled in the art may implement the functionality described by various methods for each of the specific applications. However, it shall not be construed that the determinations of the implementation deviate from the range of the contents of the present disclosure.

The description about the presented embodiments is provided so as for those skilled in the art to use or carry out the present disclosure. Various modifications of the embodiments will be apparent to those skilled in the art. General principles defined herein may be applied to other embodiments without departing from the scope of the present disclosure. Therefore, the present disclosure is not limited to the embodiments presented herein. The present disclosure shall be interpreted within the broadest meaning range consistent to the principles and new characteristics presented herein.

In an embodiment of the present disclosure, a server may also include other configurations for performing a server environment. The server may include all of the predetermined types of devices. The server is a digital device, and may be a digital device, such as a laptop computer, a notebook computer, a desk top computer, a web pad, a mobile phone, which is equipped with a processor, includes a memory, and has computing capability. The server may be a web server processing the service. The kind of foregoing server is merely an example, and the present disclosure is not limited thereto.

In the present specification, a neural network, an artificial neural network, and a network function may often be interchangeably used.

In the present disclosure, the term "image" may be used as a term meaning a medical image provided from various medical imaging apparatuses, such as Computed Tomography (CT). For example, the image may be a chest CT image taken at a predetermined time for a specific object to be examined. The foregoing example is merely illustrative, and does not limit the present disclosure, and for example, the image may be a chest CT image, a Magnetic Resonance Imaging (MRI) image, and a Positron Emission Tomography (PET) image. Each image may include one or more cross-sectional images according to each direction of photographing an object to be examined.

In the present disclosure, the term "cross-sectional image" may mean an image photographed in each direction in which an object to be examined is photographed. For example, the cross-sectional image may be used as a term indicating an axial view image, a coronal view image, or a sagittal view image. Each image photographed at a predetermined time for a predetermined object to be examined may include one or more cross-sectional images (in the present disclosure, "a first cross-sectional image," "a second cross-sectional image," and "a third cross-sectional image"), and each cross-sectional image may be, for example, any one of an axial view image, a coronal view image, or a sagittal view image according to each direction in which the object to be examined is photographed. The foregoing example is merely illustrative, and does not limit the present disclosure.

In the present disclosure, the term "nodule" may be used as a term referring to a nodule (mass, lump, and the like) existing in an object to be examined to be explored through serial images analysis. According to several embodiments of the present disclosure, a nodule may be detected from each image based on a deep learning algorithm, and a nodule data set including nodule data for the detected nodule may be generated. The foregoing example is merely illustrative, and does not limit the present disclosure.

In the present disclosure, the term "nodule data" may be used as a term referring to data for one or more nodules detected by inputting each image to the deep learning algorithm. The nodule data for each nodule may include at least one of "identification data," "location data," "segmentation data," "diameter data," "volume data,", "type classification data," "Lung-RADS score data," and "malignancy risk data" for the nodule.

The identification data may be data assigned to each nodule in order to identify each nodule, and may be an ID for each nodule, a unique number, and the like. For example, identification data, such as C0, C1, and C2, may be assigned to each of the three nodules detected from a predetermined image.

The location data may be data for a location of each nodule. For example, the location data may be a number of a cross-sectional image in which each nodule is located, or a center position of each nodule.

The segmentation data may be mask data for each nodule. For example, an area occupied by each nodule in each cross-sectional image may be highlighted mask data. In the meantime, mask data of different colors may be generated according to the depth of the shadow of each nodule observed in each cross-sectional image. For example, red mask data may be generated for an overall area of each nodule, but when a completely opaquely observed area (solid portion) exists in the area of each nodule, bright green mask data may be generated for the corresponding area.

The diameter data may be data for a diameter of each nodule, and for example, the diameter data may include data for a diameter of each nodule observed in each cross-sectional image. The diameter data of each nodule may be determined from the segmentation data of each nodule.

The volume data may be data for a volume of each nodule. The volume data of each nodule may be determined from the segmentation data of each nodule. The type classification data may be data for the type of each nodule. For example, the type classification data may be data for determining each nodule to any one of a solid type, a part-solid type, or a non-solid type according to the depth of the shadow of each nodule observed in the cross-sectional image.

The Lung-RADS score data may be data for a Lung-RADS score of each nodule. The Lung-RADS score is a score that can be determined for each nodule based on Lung-RADS® that is a tool for standardizing CT reading and management recommendations for lung cancer screening, and specifically, the Lung-RADS score may be determined from the diameter data, the volume data, or the type classification data of each nodule. For example, according to Lung-RADS Version 1.1, the solid-type nodule having a diameter less than 6 mm may be determined to have a Lung-RADS score of 2, which means the nodule that are very unlikely to develop into a cancer, and at the same time, means the nodule for which continuous screening by LDCT is recommended every year.

The malignancy risk data may be data for malignancy risk of each nodule. For example, the malignancy risk data may include data on whether each nodule is determined to be malignant (positive if the nodule is determined to be malignant, and negative when the nodule is determined to be negative) or data for a probability value that each nodule is malignant. The malignancy risk data of each nodule may be determined based on the position data, the diameter data, the volume data, the type classification data, or the like. However, the foregoing example is merely illustrative, and does not limit the present disclosure.

In the present disclosure, the term "nodule data set" is data set obtained by inputting an image to a deep learning algorithm, and may be used as a term referring to a collection of nodule data for each of the nodules existing in the input image. For example, "a first nodule data set" obtained by inputting a first image to the deep learning algorithm may include "nodule data A" for "nodule A" and "nodule data B" for "nodule B" detected from the first image, and in this case, the "nodule data A" may include at least one of identification data, location data, segmentation data, diameter data, volume data, type classification data, Lung-RADS score data, and malignancy risk data for "nodule A."

Otherwise, in the present disclosure, the term "nodule data set" may be used as a term referring to a data set generated by reflecting a user input to a data set obtained by inputting an image to the deep learning algorithm. For example, a second nodule data set including "changed nodule data A" and "nodule data B" may be generated by reflecting a user input of changing at least a part of the "nodule data A" included in the first nodule data set. The foregoing example is merely illustrative, and does not limit the present disclosure.

In the present disclosure, the term "deep learning algorithm" may be used as a term referring to one or more modules performing a series of inference process and/or inference of detecting one or more nodules from an image and generating nodule data for each of the detected nodules. In the present disclosure, the deep learning algorithm may construct a computer program stored in a memory of a server. That is, a processor of the server may read the computer program stored in the server and input an image to the deep learning algorithm, and obtain data for the detected nodule. Further, the server may generate a user interface by transmitting the obtained data to a user's equipment. However, the present disclosure is not limited thereto, and the deep learning algorithm may construct a computer program stored in a memory of a user's equipment. That is, the user's equipment may obtain data for a nodule existing in an image through the deep learning algorithm, and generate a user interface based on the obtained data.

According to several embodiments of the present disclosure, the deep learning algorithm may include at least one of "a nodule detection module," "a nodule measurement module," and "a nodule classification module."

The nodule detection module may detect one or more nodules based on the input image, and obtain location data of the detected nodule.

The nodule measurement module may obtain segmentation data of the nodule based on the location data of the nodule. Otherwise, the nodule measurement module may obtain diameter data and volume data of the nodule based on the location data and the segmentation data of the nodule.

The nodule type classification module may obtain type classification data of the nodule based on the location data and the segmentation data of the nodule. Otherwise, the nodule type classification module may obtain Lung-RADS score data and/or malignancy risk data of the nodule based on the diameter data, the volume data, and the type classification data of the nodule. However, the foregoing example is merely illustrative, and does not limit the present disclosure.

In the present disclosure, the term "nodule information" is generated based on the nodule data set, and may be used as a term referring to an object displayed on an image on the user interface according to several embodiments of the present disclosure. For example, "nodule information A" for "nodule A" and "nodule information B" for "nodule B" may be generated based on the first nodule data set, and displayed on the first image on the user interface.

In the meantime, the "nodule information" may be "candidate nodule information" or determined "first nodule information."

The "candidate nodule information" may be nodule information generated from the nodule data set obtained through the deep learning algorithm of the server and displayed as an initial value on the image of the user interface. For example, when a first image is first displayed in the user's equipment, the candidate nodule information may be nodule information displayed as an initial value together with the first image.

On the contrary, the determined "first nodule information" may be determined as nodule information in which the "candidate nodule information" is related to the image based on the user's input. For example, based on whether the user's input is input, and/or the content of the user input, the "candidate nodule information" may be determined as the "first nodule information" as it is, the changed "candidate nodule information" may be determined as the "first nodule information," or, it may be determined that the "candidate nodule information" is not the "first nodule information." The foregoing example is merely illustrative, and does not limit the present disclosure.

In the meantime, the "nodule information" may be generated to be associated with "nodule detailed information" which is to be described below.

In the present disclosure, the term "nodule detailed information" is generated to be associated with the "nodule information" based on the nodule data set, and may be used as a term referring to an object displayed on the user interface according to the several embodiments of the present disclosure. For example, based on "the first nodule data set," "nodule detailed information A" may be generated so as to be associated with "nodule information A" for "nodule A," and "nodule detailed information B" may be generated so as to be associated with "nodule information B" for "nodule B."

The nodule detailed information may be linked with the associated nodule information. For example, the user may input the user input for "nodule information A" through "nodule information A" or "nodule detailed information A." That is, based on the user input through "nodule detailed information A," "nodule information A" associated with "nodule detailed information A" may be determined as nodule information related to the first image. The foregoing example is merely illustrative, and does not limit the present disclosure.

In the meantime, the "nodule detailed information" may be displayed in an area different from that of the "nodule information" on the user interface. For example, the "nodule information" is displayed in a first area of the user interface, the "nodule detailed information" may be displayed in a second area that is different from the first area. However, the present disclosure is not limited thereto.

In the present disclosure, the term "user input" may be a predetermined type of user input on the user interface. For example, the user input may be performed for the purpose of reviewing the nodule data obtained through the deep learning algorithm. The nodule detected by inputting the image to the deep learning algorithm may be different from the nodule actually existing in the image. For example, the nodule detected through the deep learning algorithm may be the nodule that does not actually exist in the image (FP), on the contrary, the nodule that is not detected through the deep learning algorithm may be the nodule actually existing in the image (FN), or the nodule detected through the deep learning algorithm is the nodule actually existing in the image (TP), but it is necessary to change at least a part of the data obtained through the deep learning algorithm for the nodule. That is, accuracy of the nodule data value (that is, accuracy of the image reading) may be increased by changing and/or fixing the nodule data obtained through the deep learning algorithm through the user input.

In particular, the "user input" may be the user input for determining "candidate nodule information" (that is, the nodule information obtained through the deep learning algorithm and displayed as an initial value on the user interface) as "first nodule information" related to "the first image" (that is, the nodule information determined to be related with the "first image" according to the user input). The "user input" may be a "change input" for changing at least a part of the candidate nodule information and/or a "confirmation input" for fixing the candidate nodule information.

The "change input" may be the user input for changing at least a part of the candidate nodule information associated with the change input. That is, in the case where the candidate nodule information generated from the nodule data set obtained through the deep learning algorithm of the server and displayed as the initial value corresponds to the nodule actually existing in the first image, but it is necessary to change a value of a part of the data (for example, the diameter data and the segmentation data), the user may change the candidate nodule information associated with the change input through the change input, and the changed candidate nodule information may be determined as the first nodule information related to the first image. However, the present disclosure is not limited thereto.

The "confirmation input" may be the user input for confirming candidate nodule information associated with the confirmation input. That is, when the candidate nodule information generated from the nodule data set obtained through the deep learning algorithm of the server and displayed as the initial value corresponds to the nodule actually existing in the first image and the data value does not need to be changed, the user may determine the candidate nodule information associated with the confirmation input as the first nodule information associated with the first image through the confirmation input. However, the present disclosure is not limited thereto.

In the meantime, as described above, the "user input" may be received through the nodule information and/or the nodule detailed information. For example, the "user input" may be a click or drag-and-drop for the nodule information and/or the nodule detailed information, or any other possible form of input. However, the present disclosure is not limited thereto, the "user input" may be a click or drag-and-drop for a graphic element (a pointer, a mask image, and the like) included in the nodule information and/or the nodule detailed information or a corresponding graphic element (checkbox, icon, input window, and the like), an input of a value, or any other possible form of user input. The foregoing example is merely the embodiment, and does not limit the present disclosure.

FIG. 1 is a block diagram illustrating a computing device for providing a user interface for serial images analysis according to several embodiments of the present disclosure.

The configuration of a computing device 100 illustrated in FIG. 1 is merely a simplified example. In the embodiment of the present disclosure, the computing device 100 may include other configurations for performing a computing environment of the computing device 100, and only some of the disclosed configurations may also configure the computing device 100.

The computing device 100 according to the embodiment of the present disclosure may include a network unit 110, a processor 120, a memory 130, an output unit 140, and an input unit 150.

The computing device 100 according to the embodiments of the present disclosure may include a Personal Computer (PC), a notebook computer, a mobile terminal, a smart phone, a tablet PC, and the like, and may include all kinds of equipment which are capable of accessing a wired/wireless network.

The network unit 110 according to the embodiments of the present disclosure may use a predetermined form of wire or wireless communication systems.

The network unit 110 in the present disclosure may be configured regardless of its communication mode, such as a wired mode and a wireless mode, and may be configured of various communication networks, such as a Personal Area Network (PAN) and a Wide Area Network (WAN). Further, the network may be the publicly known World Wide Web (WWW), and may also use a wireless transmission technology used in PAN, such as Infrared Data Association (IrDA) or Bluetooth.

The technologies described in the present specification may be used in other networks, as well as the foregoing networks.

The processor 120 according to the embodiment of the present disclosure may consist of one or more cores, and may include a processor, such as a Central Processing Unit (CPU), a General Purpose Graphics Processing Unit (GPGPU), and a Tensor Processing Unit (TPU) of the computing device, for analyzing data, deep learning, and/or providing a user interface. The processor 120 may read a computer program stored in the memory 130 and perform data processing for machine learning and/or provide a user interface according to the embodiment of the present disclosure. According to the embodiment of the present disclosure, the processor 120 may perform computation for training a neural network. The processor 120 may perform a calculation, such as processing of input data for training in Deep Learning (DN), extraction of a feature from input data, an error calculation, and updating of a weight of the neural network by using backpropagation, for training the neural network. At least one of the CPU, GPGPU, and TPU of the processor 120 may process training of a network function. For example, the CPU and the GPGPU may process training of the network function and data classification by using a network function together. Further, in the embodiment of the present disclosure, the training of the network function and the data classification by using a network function may be processed by using the processors of the plurality of computing devices together. Further, the computer program executed in the computing device according to the embodiment of the present disclosure may be a CPU, GPGPU, or TPU executable program.

The memory 130 according to the embodiment of the present disclosure may store the predetermined form of information generated or determined by the processor 120 and the predetermined form of information received by the network unit 110.

According to the embodiment of the present disclosure, the memory 130 may include at least one type of storage medium among a flash memory type, a hard disk type, a multimedia card micro type, a card type of memory (for example, an SD or XD memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disk, and an optical disk. The computing device 100 may also be operated in relation to web storage performing a storage function of the memory 130 on the Internet. The description of the foregoing memory is merely illustrative, and the present disclosure is not limited thereto.

The output unit 140 according to the embodiment of the present disclosure may display a user interface according to the embodiment of the present disclosure. The output unit 140 may display the user interface as illustrated in FIGS. 3, 4, 6 to 8, 10, and 11. The user interfaces which will be illustrated and described below are merely examples, and the present disclosure is not limited thereto.

The output unit 140 according to the embodiment of the present disclosure may output the predetermined form of information generated or determined by the processor 120 and the predetermined form of information received by the network unit 110.

In the embodiment of the present disclosure, the output unit 140 may include at least one of a Liquid Crystal Display (LCD), a Thin Film Transistor Liquid Crystal Display (TFT LCD), an Organic Light Emitting Diode (OLED), a flexible display, and a 3D display. Some display modules among them may be formed of a transparent or light transmissive type so that the outside may be viewed through the display modules. This may be referred to as a transparent display module, and a representative example of the transparent display module includes a Transparent OLED (TOLED).

A user input may be received through the input unit 150 according to the embodiment of the present disclosure. The input unit 150 according to the embodiment of the present disclosure may be provided with keys and/or buttons for receiving a user input. The computer program for providing the user interface according to the embodiment of the present disclosure may be executed according to a user input through the input unit 150.

The input unit 150 according to the embodiments of the present disclosure may receive a signal by detecting a button manipulation or a touch input of a user or receive a voice or an operation of a user and the like through a camera or a microphone and convert the received signal, voice, or operation to an input signal. To this end, speech recognition technology or motion recognition technology may be used.

The input unit 150 according to the embodiments of the present disclosure may also be implemented as external input equipment connected with the computing device 100. For example, the input equipment may be at least one of a touch pad, a touch pen, a keyboard, and a mouse for receiving a user input, but this is merely an example, and the present disclosure is not limited thereto.

The input unit 150 according to the embodiments of the present disclosure may recognize a touch input of a user. The input unit 150 according to the embodiments of the present disclosure may have the same configuration as that of the output unit 140. The input unit 150 may be formed of a touch screen implemented so as to receive a selection input of a user. In the touch screen, any one of a contact type capacitance method, an infrared light sensing method, a Surface Ultrasonic Wave (SAW) method, a piezoelectric method, and a resistive film method may be used. The detailed description for the foregoing touch screen is merely illustrative according to the embodiments of the present disclosure, and various touch screen panels may be applied to the computing device 100. The input unit 150 formed of a touch screen may include a touch sensor. The touch sensor may be configured to convert a change in pressure applied to a specific region of the input unit 150 or electrostatic capacity generated in a specific region of the input unit 150 into an electric input signal. The touch sensor may be configured so as to detect pressure of a touch, as well as a location and an area of a touch. When a touch input is made to the touch sensor, a signal(s) corresponding to the touch input is transmitted to a touch controller. The touch controller processes the signal(s) and then transmits data corresponding to the signal(s) to the processor 120. Accordingly, the processor 120 may recognize a touched region of the input unit 150 and the like.

The server (not illustrated) according to the embodiment of the present disclosure may also include other configurations for executing a server environment of the server. The server may include all of the predetermined types of devices. The server is a digital device, and may be a digital device, such as a laptop computer, a notebook computer, a desk top computer, a web pad, a mobile phone, which is equipped with a processor, includes a memory, and has computing capability.

The server for performing the operation of providing a user equipment with the user interface for serial images analysis according to the embodiment of the present disclosure may include a network unit, a processor, and a memory.

The server may obtain a nodule data set for generating a user interface according to the embodiments of the present disclosure and/or generate a user interface based on the obtained nodule data set. The server may be a computing system which provides a client (for example, a user equipment) with information through a network. The server may transmit the image and/or the nodule data set obtained from the image to the user equipment, or generate a user interface based on the obtained nodule data set and transmit the generated user interface to the user equipment. In this case, the user equipment may be a predetermined form of computing device 100 which is capable of accessing the server. The processor of the server may transmit the image and the nodule data set related to the image to the user equipment through the network unit, or transmit the user interface generated based on the nodule data set. The server according to the embodiments of the present disclosure may be, for example, a cloud server. The server may be a web server processing the service. The kind of foregoing server is merely an example, and the present disclosure is not limited thereto.

Each of the network unit, the processor, and the memory included in the server according to the embodiments of the present disclosure may perform the same roles as those of the network unit 110, the processor 120, and the memory 130 included in the computing device 100 or be identically configured to the network unit 110, the processor 120, and the memory 130 included in the computing device 100.

In the embodiments of the present disclosure, the areas may be spaces displayed on the user interface and not-overlapping on a screen. Otherwise, two or more areas may also be displayed while overlapping. In the case where two or more areas are displayed while overlapping, one area may be hidden by another area and not be viewed. Otherwise, in the case where two or more areas are displayed while overlapping and an upper area is partially semi-transparently displayed, at least a part of a lower area may be viewed. Two or more areas may have the same size. Further, two or more areas may also have the different sizes. One area may also include only one area, or may also include a plurality of sub areas. One area may include one or more display objects.

In the embodiments of the present disclosure, the object may be a set of a picture, a symbol, or a character corresponding to each of a program, a command, and data. According to the embodiments of the present disclosure, the object may be used for receiving a user selection input. For example, when a user input for an object is received, the processor 120 may execute a command or data stored in correspondence to the corresponding object and display the command or the data in the user interface. In the embodiments of the present disclosure, the object and the display object may be interpreted as the same meaning.

In the embodiments of the present disclosure, "display" may be an operation for displaying data to the user through the output unit 140. "Display" and "display" may be interchangeably used.

Hereinafter, a method of providing a user interface for serial images analysis according to embodiments of the present disclosure will be described.

Figure 2:
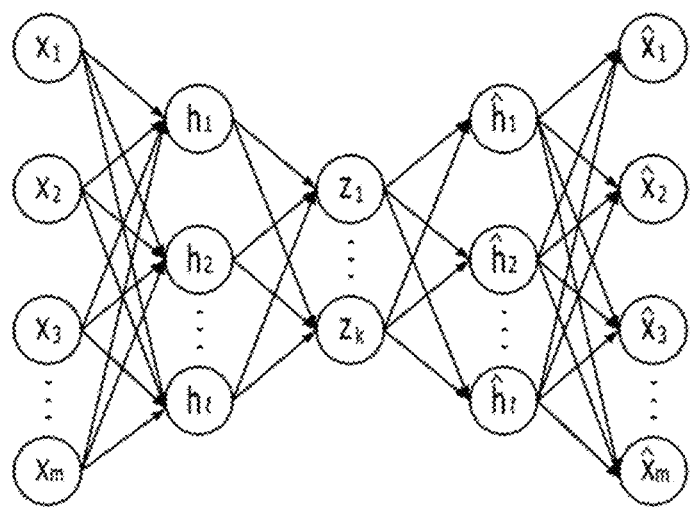
FIG. 2 is a schematic diagram illustrating a network function according to the embodiment of the present disclosure.

FIG. 2 is a schematic diagram illustrating a network function according to the embodiment of the present disclosure.

Throughout the present specification, a calculation model, a nerve network, the network function, and the neural network may be used interchangeably. For example, each of one or more modules configuring the deep learning algorithm in the present disclosure may be operated based on the neural network which is to be described in detail below.

The neural network may be formed of a set of interconnected calculation units which are generally referred to as "nodes." The "nodes" may also be called "neurons." The neural network consists of one or more nodes. The nodes (or neurons) configuring the neural network may be interconnected by one or more links.

In the neural network, one or more nodes connected through the links may relatively form a relationship of an input node and an output node. The concept of the input node is relative to the concept of the output node, and a predetermined node having an output node relationship with respect to one node may have an input node relationship in a relationship with another node, and a reverse relationship is also available. As described above, the relationship between the input node and the output node may be generated based on the link. One or more output nodes may be connected to one input node through a link, and a reverse case may also be valid.

In the relationship between an input node and an output node connected through one link, a value of the output node data may be determined based on data input to the input node. Herein, a link connecting the input node and the output node may have a weight. The weight is variable, and in order for the neural network to perform a desired function, the weight may be varied by a user or an algorithm. For example, when one or more input nodes are connected to one output node by links, respectively, a value of the output node may be determined based on values input to the input nodes connected to the output node and weights set in the link corresponding to each of the input nodes.

As described above, in the neural network, one or more nodes are connected with each other through one or more links to form a relationship of an input node and an output node in the neural network. A characteristic of the neural network may be determined according to the number of nodes and links in the neural network, a correlation between the nodes and the links, and a value of the weight assigned to each of the links. For example, when there are two neural networks in which the numbers of nodes and links are the same and the parameter values between the links are different, the two neural networks may be recognized to be different from each other.

The neural network may consist of a set of one or more nodes. A subset of the nodes forming the neural network may form a layer. Some of the nodes configuring the neural network may form one layer based on distances from an initial input node. For example, a set of nodes having a distance of n from an initial input node may form n layers. The distance from the initial input node may be defined by the minimum number of links, which need to be passed from the initial input node to a corresponding node. However, the definition of the layer is arbitrary for the description, and a degree of the layer in the neural network may be defined by a different method from the foregoing method. For example, the layers of the nodes may be defined by a distance from a final output node.

The initial input node may mean one or more nodes to which data is directly input without passing through a link in a relationship with other nodes among the nodes in the neural network. Otherwise, the initial input node may mean nodes which do not have other input nodes connected through the links in a relationship between the nodes based on the link in the neural network. Similarly, the final output node may mean one or more nodes that do not have an output node in a relationship with other nodes among the nodes in the neural network. Further, the hidden node may mean nodes configuring the neural network, not the initial input node and the final output node.

In the neural network according to the embodiment of the present disclosure, the number of nodes of the input layer may be the same as the number of nodes of the output layer, and the neural network may be in the form that the number of nodes decreases and then increases again from the input layer to the hidden layer. Further, in the neural network according to another embodiment of the present disclosure, the number of nodes of the input layer may be smaller than the number of nodes of the output layer, and the neural network may be in the form that the number of nodes decreases from the input layer to the hidden layer. Further, in the neural network according to another embodiment of the present disclosure, the number of nodes of the input layer may be larger than the number of nodes of the output layer, and the neural network may be in the form that the number of nodes increases from the input layer to the hidden layer. The neural network according to another embodiment of the present disclosure may be the neural network in the form in which the foregoing neural networks are combined.

A deep neural network (DNN) may mean the neural network including a plurality of hidden layers, in addition to an input layer and an output layer. When the DNN is used, it is possible to recognize a latent structure of data. That is, it is possible to recognize latent structures of photos, texts, videos, voice, and music (for example, what objects are in the photos, what the content and emotions of the texts are, and what the content and emotions of the voice are). The DNN may include a convolutional neural network (CNN), a recurrent neural network (RNN), an auto encoder, Generative Adversarial Networks (GAN), a restricted Boltzmann machine (RBM), a deep belief network (DBN), a Q network, a U network, a Siamese network, and the like. The foregoing description of the deep neural network is merely illustrative, and the present disclosure is not limited thereto.

In the embodiment of the present disclosure, the network function may include an auto encoder. The auto encoder may be one type of artificial neural network for outputting output data similar to input data. The auto encoder may include at least one hidden layer, and the odd-numbered hidden layers may be disposed between the input/output layers. The number of nodes of each layer may decrease from the number of nodes of the input layer to an intermediate layer called a bottleneck layer (encoding), and then be expanded symmetrically with the decrease from the bottleneck layer to the output layer (symmetric with the input layer). The auto encoder may perform a nonlinear dimension reduction. The number of input layers and the number of output layers may correspond to the dimensions after preprocessing of the input data. In the auto encoder structure, the number of nodes of the hidden layer included in the encoder decreases as a distance from the input layer increases. When the number of nodes of the bottleneck layer (the layer having the smallest number of nodes located between the encoder and the decoder) is too small, the sufficient amount of information may not be transmitted, so that the number of nodes of the bottleneck layer may be maintained in a specific number or more (for example, a half or more of the number of nodes of the input layer and the like).

The neural network may be trained by at least one scheme of supervised learning, unsupervised learning, semi-supervised learning, and reinforcement learning. The training of the neural network may be a process of applying knowledge for the neural network to perform a specific operation to the neural network.

The neural network may be trained in a direction of minimizing an error of an output. In the training of the neural network, training data is repeatedly input to the neural network and an error of an output of the neural network for the training data and a target is calculated, and the error of the neural network is back-propagated in a direction from an output layer to an input layer of the neural network in order to decrease the error, and a weight of each node of the neural network is updated. In the case of the supervised learning, training data labelled with a correct answer (that is, labelled training data) is used, in each training data, and in the case of the unsupervised learning, a correct answer may not be labelled to each training data. That is, for example, the training data in the supervised learning for data classification may be data, in which category is labelled to each of the training data. The labelled training data is input to the neural network and the output (category) of the neural network is compared with the label of the training data to calculate an error. For another example, in the case of the unsupervised learning related to the data classification, training data that is the input is compared with an output of the neural network, so that an error may be calculated. The calculated error is back-propagated in a reverse direction (that is, the direction from the output layer to the input layer) in the neural network, and a connection weight of each of the nodes of the layers of the neural network may be updated according to the backpropagation. A variation rate of the updated connection weight of each node may be determined according to a learning rate. The calculation of the neural network for the input data and the backpropagation of the error may configure a learning epoch. The learning rate is differently applicable according to the number of times of repetition of the learning epoch of the neural network. For example, at the initial stage of the learning of the neural network, a high learning rate is used to make the neural network rapidly secure performance of a predetermined level and improve efficiency, and at the latter stage of the learning, a low learning rate is used to improve accuracy.

In the learning of the neural network, the training data may be generally a subset of actual data (that is, data to be processed by using the learned neural network), and thus an error for the training data is decreased, but there may exist a learning epoch, in which an error for the actual data is increased. Overfitting is a phenomenon, in which the neural network excessively learns training data, so that an error for actual data is increased. For example, a phenomenon, in which the neural network learning a cat while seeing a yellow cat cannot recognize cats, other than a yellow cat, as cats, is a sort of overfitting. Overfitting may act as a reason of increasing an error of a machine learning algorithm. In order to prevent overfitting, various optimizing methods may be used. In order to prevent overfitting, a method of increasing training data, a regularization method, a dropout method of inactivating a part of nodes of the network during the learning process, a method using a bath normalization layer, and the like may be applied.

Figure 3:
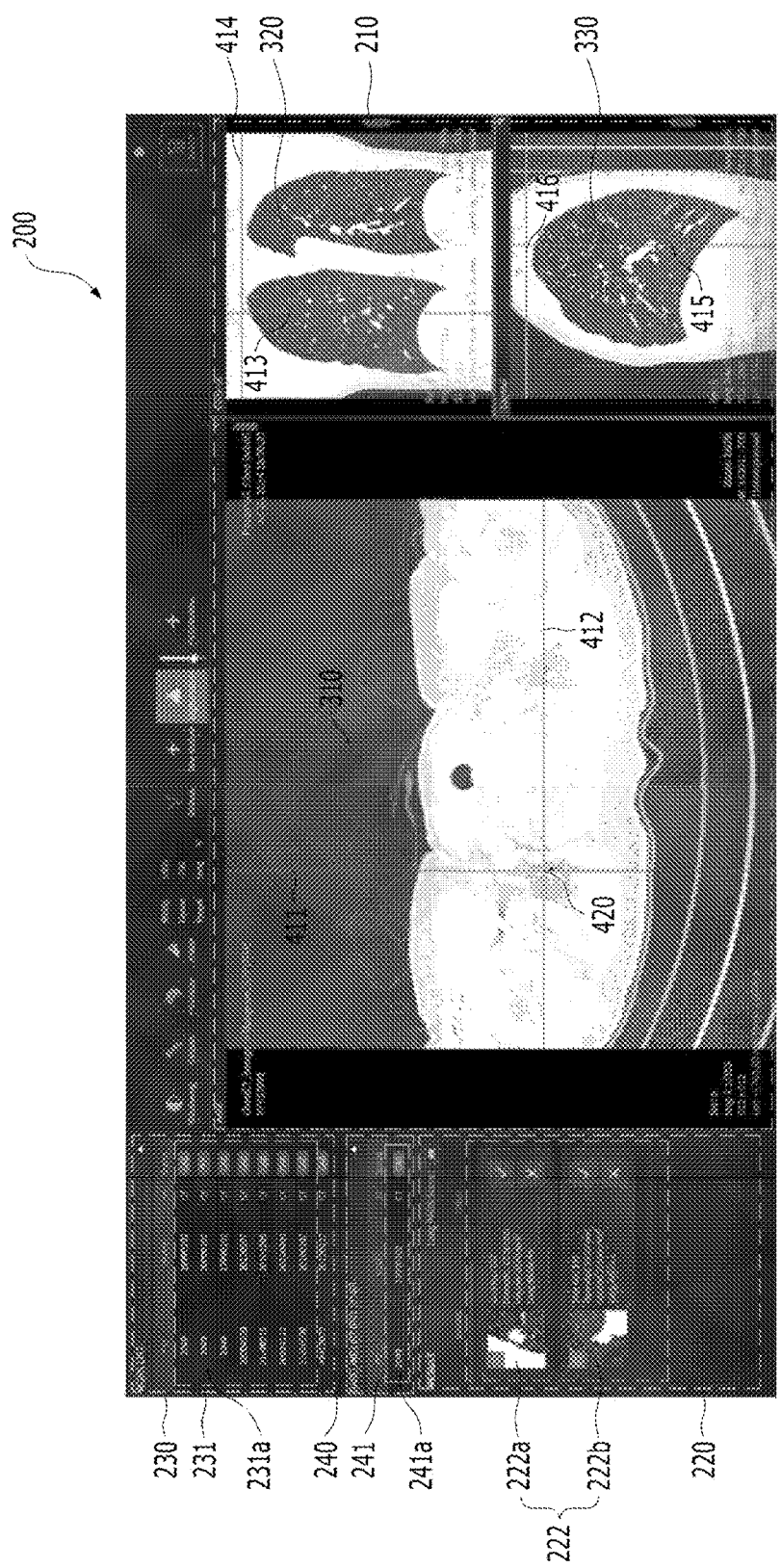
FIG. 3 is a diagram illustrating an example of a first area to a fourth area that may configure the user interface for serial images analysis according to several embodiments of the present disclosure.

FIG. 3 is a diagram illustrating an example of a first area to a fourth area that may configure the user interface for serial images analysis according to several embodiments of the present disclosure.

Figure 4:
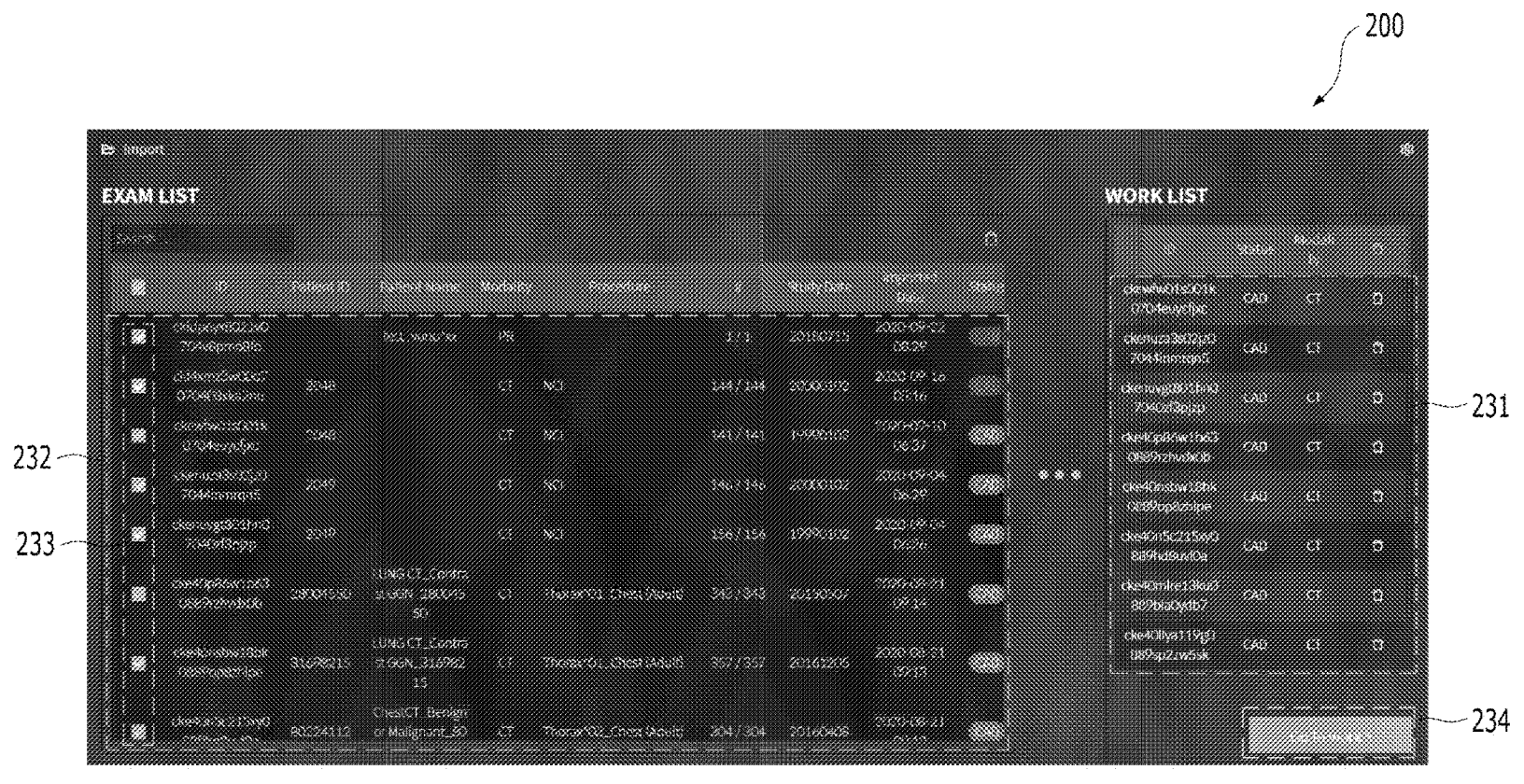

FIG. 4 is a diagram illustrating an example of a user interface for generating an image list according to several embodiments of the present disclosure. Referring to FIG. 3, a user interface 200 may include a first area 210 for displaying at least one image and nodule information related to the image, a second area 220 for displaying nodule detailed information 222 (222a, 222b) associated with the nodule information, a third area 230 for displaying an image list 231, and a fourth area 240 for displaying a list of related images for the image selected from the image list. The processor 120 may control the output unit 140 so as to display the first area 210 for displaying at least one image and nodule information related to the image, the second area 220 for displaying the nodule detailed information 222 associated with the nodule information, the third area 230 for displaying the image list 231, and the fourth area 240 for displaying a list 241 of the related images for an image 231a selected from the image list 231. Further, the processor 120 may receive at least one image to be displayed in each area and a nodule data set related to the image from the server through the network unit 110. However, the foregoing constituent elements are not essential in implementing the user interface 200, so the user interface 200 may have more or fewer constituent elements that those listed above.

The first area 210 may display at least one cross-sectional image related to at least one image. In the meantime, the first area 210 may display nodule information related to at least one image and receive a user input. The processor 120 may control the output unit 140 so as to display at least one cross-sectional image related to at least one image and nodule information related to at least one image. Further, the processor 120 may control the input unit 150 so as to receive the user input on the first area 210.

FIG. 3 illustrates an example in which three cross-sectional images 310, 320, and 330 related to the first image 213a are displayed in the first area 210.

More particularly, according to several embodiments of the present disclosure illustrated in FIG. 3, the first area 210 may display an axial view image 310, a coronal view image 320, or a sagittal view image 330 related to the first image 231a. For example, the three cross-sectional images 310, 320, and 330 may be displayed in sub areas, respectively, by dividing the first area 210 into the three sub areas.

In this case, the first area 210 may further display a first indicative line 411 and a second indicative line 412 on the first cross-sectional image 310, a third indicative line 413 and a fourth indicative line 414 on the second cross-sectional image 320, and a fifth indicative line 415 and a sixth indicative line 416 on the third cross-sectional image 330.

In the meantime, a first reference indication 420 for identifying, by the user, a point of interest may be further displayed on the first cross-sectional image 310, and the first reference indication 420 may be configured to include a crossing point of the first indicative line 411 and the second indicative line 412 which cross each other. The first reference indication 420 may move on the first cross-sectional image 310 in response to the user input.

In the meantime, the first indicative line 411 may move while being linked with the third indicative line 413, and the second indicative line 412 may move while being linked with the fifth indicative line 415. According to the movement of the first indicative line 411, the displayed third cross-sectional image 330 may be different. Otherwise, according to the movement of the second indicative line 412, the displayed second cross-sectional image 320 may be different.

In the meantime, the fourth indicative line 414 may move while being linked with the sixth indicative line 416. According to the movement of the fourth indicative line 414 and the sixth indicative line 416, the displayed first cross-sectional image 310 may be different.

An element (for example, a scroll bar) representing depth information of the first cross-sectional image 310 may be displayed on the first cross-sectional image 310. For example, when the user moves the scroll bar in the vertical direction on the first cross-sectional image 310, the displayed first cross-sectional image 310 is changed and simultaneously, the fourth indicative line 414 on the second cross-sectional image 320 and the sixth indicative line 416 on the third cross-sectional image 330 may also move vertically according to the change of the first cross-sectional image 310. However, the present disclosure is not limited thereto, and the element, such as the scroll bar, representing the depth information of the cross-sectional image may also be displayed on the second cross-sectional image 320 and/or the third cross-sectional image 330, and implement the foregoing operation. For example, when the user moves the scroll bar in the vertical direction on the second cross-sectional image 320, the displayed second cross-sectional image 320 is changed, and at the same time, the second indicative line 412 may move in the vertical direction, and the fifth indicative line 415 may move in the horizontal direction. Otherwise, when the user moves the scroll bar in the vertical direction on the third cross-sectional image 330, the displayed third cross-sectional image 330 is changed, and at the same time, the first indicative line 411 and the third indicative line 413 may move in the horizontal direction.

FIG. 3 illustrates an example in which the first indicative line 411 to the sixth indicative line 416 according to several embodiments of the present disclosure are displayed as solid lines. However, the present disclosure is not limited thereto, and for example, the indicative line may be displayed in a predetermined form of line, such as a solid line and a dotted line, or may be displayed in the form of a figure, other than a line. Further, a length of the indicative line according to several embodiments of the present disclosure may correspond to a height and/or a width of each cross-sectional image or may be displayed to be shorter or longer than a height and/or a width of each cross-sectional image. The content of the form of the indicative line is merely an example, and does not limit the present disclosure.

In the meantime, at least one of the first cross-sectional image 310, the second cross-sectional image 320, and the third cross-sectional image 330 may be manipulated according to the input of the user. For example, at least one of the first cross-sectional image 310, the second cross-sectional image 320, and the third cross-sectional image 330 may be zoomed in or zoomed out, has changed brightness, or a size of an area of each cross-sectional image occupied in the first area 210 may be changed. Otherwise, the first cross-sectional image 310, the second cross-sectional image 320, and the third cross-sectional image 330 may be manipulated so that only any one of the first cross-sectional image 310, the second cross-sectional image 320, and the third cross-sectional image 330 is displayed on the first area 210 according to the input of the user. The foregoing example is merely illustrative, and does not limit the present disclosure.

The second area 220 may display the nodule detailed information 222 associated with the nodule information and receive the user input. The processor 120 may control the output unit 140 so as to display the nodule detailed information 222 associated with the nodule information. Further, the processor 120 may control the input unit 150 so as to receive the user input on the second area 210.

The nodule detailed information 222 may be generated based on the first nodule data set, and each nodule detailed information 222 may include more items of nodule data than the associated nodule information. For example, when the nodule information includes segmentation data and diameter data, the nodule detailed information corresponding to the nodule information may additionally include volume data, Lung-RADS score data, and/or malignancy risk data, in addition to the segmentation data and the diameter data. That is, the nodule detailed information 222 may provide a user with more detailed information about each nodule, compared to the corresponding nodule information. However, the present disclosure is not limited thereto.

In the meantime, FIG. 3 illustrates the example in which two or more nodule detailed information 222 displayed on the second area 220 are aligned in a list form, but the present disclosure is not limited thereto, and the nodule detailed information may be aligned in various methods, such as a checkerboard.

In the meantime, the second area 220 may additionally display a representative value of the nodule detailed information 222. For example, the largest Lung-RADS score value among the Lung-RADS score data values included in each nodule detailed information may be separately displayed at an upper end of the second area 220. The foregoing example is merely illustrative, and does not limit the present disclosure.

The first area 210 and the second area 220 will be described below in more detail with reference to FIGS. 5 to 10.

The third area 230 may display the image list 231 including the first image and receive a selection of the user for the first image 231a. The processor 120 may control the output unit 140 so as to display the image list 231 including the first image. Further, the processor 120 may control the input unit 150 so as to receive a selection of the user for the first image 231a on the third area 230.

The image list 231 may include all of the photographed images, the image that is input to the deep learning algorithm after being photographed to obtain the nodule data set, or one or more images selected by the user.

Referring to FIG. 4, the image list 231 may be configured to include one or more images selected (for example, selected by clicking a check box 233 corresponding to each image) by the user from the entire image list 232. Further, referring to FIG. 4, the image list 231 may be displayed on the third area 230 by clicking a "Go to work" icon 234.

The selection of the user for the first image 231a may be a click for the first image 231a on the image list 231. However, the present disclosure is not limited thereto, and the selection of the user for the first image 231a may be a click for a graphic element (a check box, an icon, and the like) corresponding to the first image 231a, or a predetermined image (for example, the most recently photographed image, the image most recently displayed on the first area 210, or an image arbitrarily designated by the user) in the image list 231 may be automatically selected. However, the present disclosure is not limited thereto.

In response to the selection of the user for the first image 231a, the first area 210 may display three cross-sectional images 310, 320, and 330 related to the first image 231a and candidate nodule information related to the first image 231a. This will be described in more detail with reference to FIGS. 5 to 8.

In the meantime, in response to the selection for the first image 231a, the fourth area 240 for displaying the list 241 of the related images for the first image 231a may be rendered. The processor 120 may control the output unit 140 so as to display the fourth area 240 which displays the list 241 of the related images related to the first image 231a in response to the selection of the user for the first image 231a input through the input unit 150.

The fourth area 240 may display the list 241 of the related images of the first image 231a, and allow a comparative selection input of the user for the second image 241a that is any one of the related images. The processor 120 may control the output unit 140 so as to display the list 241 of the related images including the second image 241a. Further, the processor 120 may control the input unit 150 so as to receive the selection input of the user for the second image 241a on the fourth area 240.

The related image may be the image photographed at a different time from that of the first image 231a for the same object to be photographed as that of the first image 231a.

More particularly, the related image may be the image photographed before the photographing time of the first image 231a for the same object to be photographed as that of the first image 231a. For example, in the case where there is an image (hereinafter, referred to as "image M") photographed in December 2020 and an image (hereinafter, referred to as "image N") photographed in December 2019 for HONG, Gil-Dong who is the object to be photographed, and image M is the first image 231a, image N may be the related image of the image M.

The list 241 of the related images may be formed of at least one related image searched in all of the photographed images, the images which are input to the deep learning algorithm after photographing and from which the nodule data set is obtained, or the images included in the image list 231.

The comparative selection input may be a click on the second image 241a in the list 241 of the related images. However, the present disclosure is not limited thereto, and the comparative selection input may be a click on a graphic element (a checkbox, an icon, and the like) corresponding to the second image 241a, or a predetermined image (for example, the most recently photographed image among the related images, the image most recently displayed in the first area 210, or an image arbitrarily designated by the user) in the list 241 of the related images may be automatically selected.

In response to the comparative selection input of the user for the second image 241a, the first image 210 displays a first cross-sectional image for comparison 340 related to the first image 231a and a second cross-sectional image for comparison 350 related to the second image 241a. This will be described in more detail with reference to FIG. 10.

Figure 5:
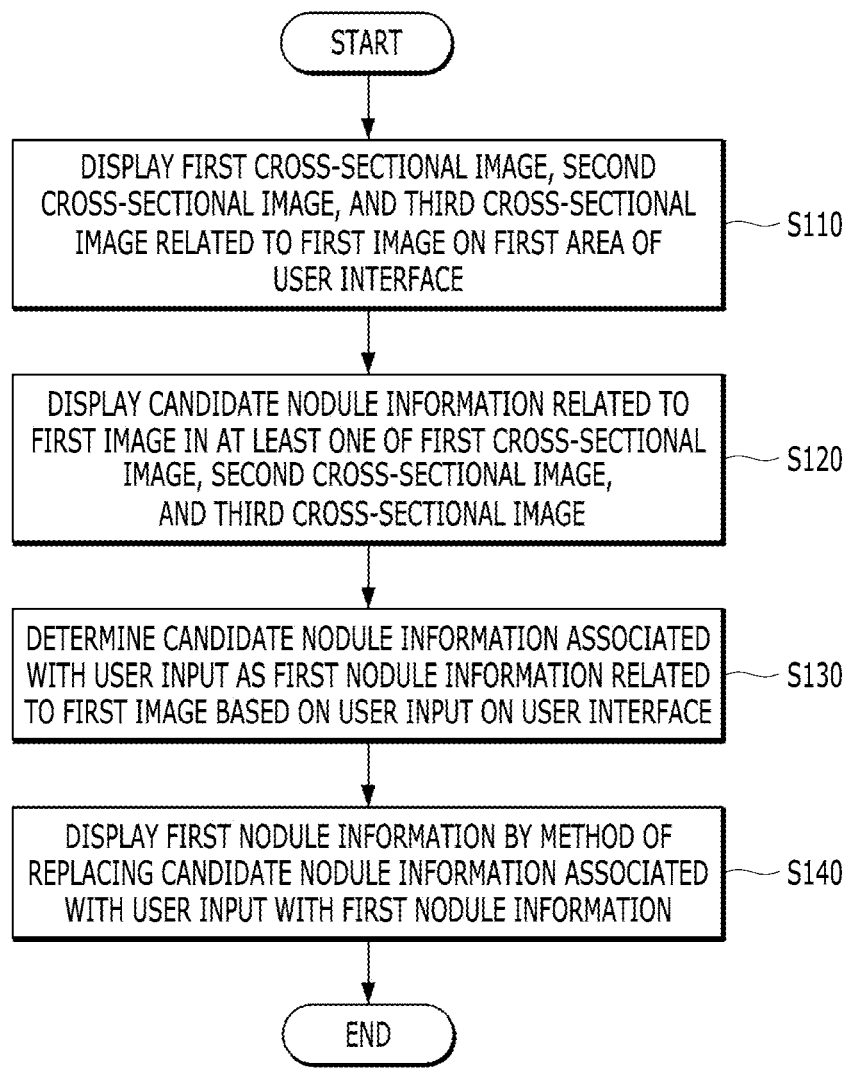
FIG. 5 is a flowchart for providing the user interface for serial images analysis according to several embodiments of the present disclosure.

FIG. 5 is a flowchart for providing the user interface for serial images analysis according to several embodiments of the present disclosure.

Figure 6:
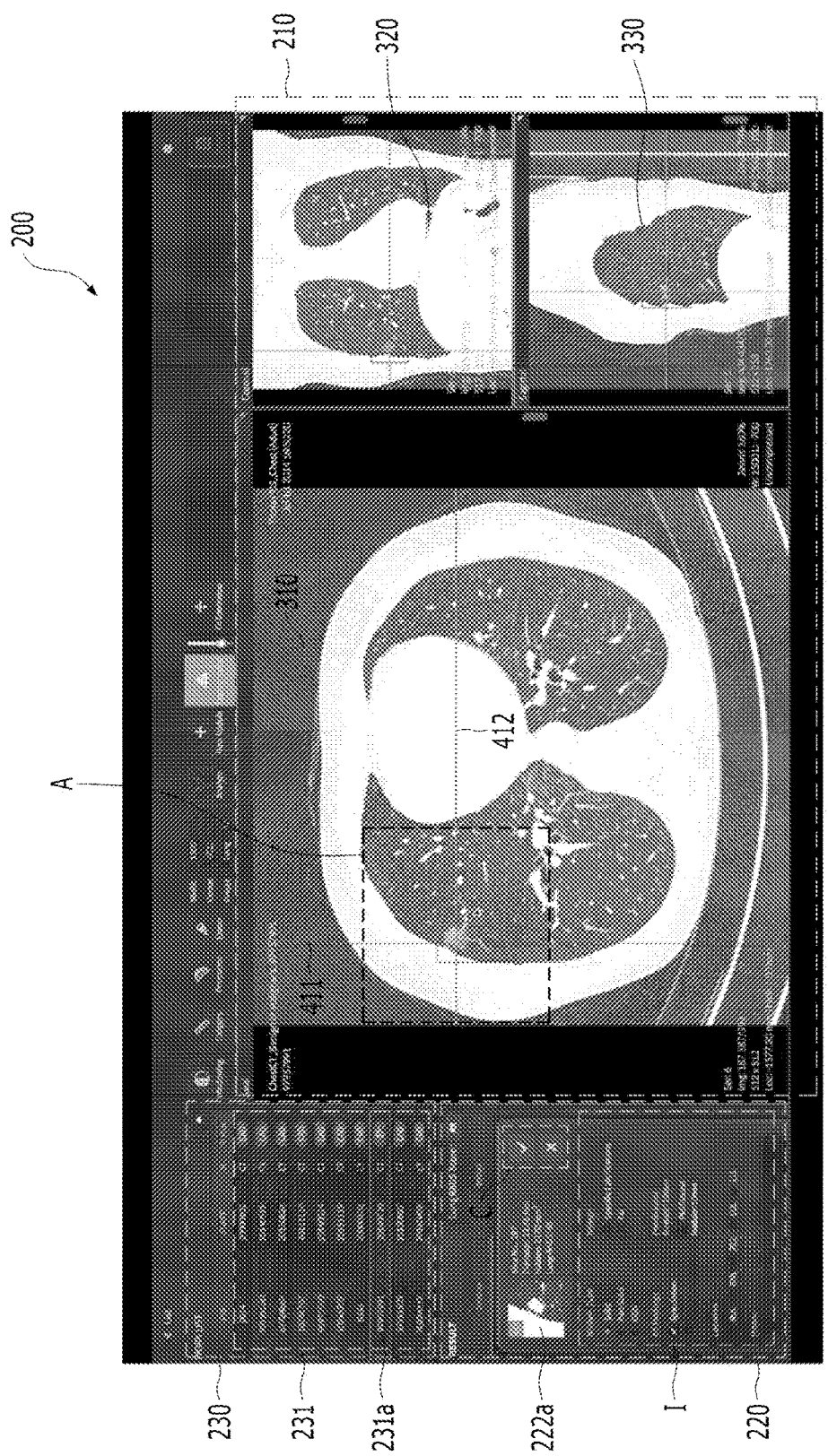
FIG. 6 is a diagram illustrating the user interface for serial images analysis according to several embodiments of the present disclosure.

FIG. 6 is a diagram illustrating an example of the user interface for serial images analysis according to several embodiments of the present disclosure.

Figure 7A:
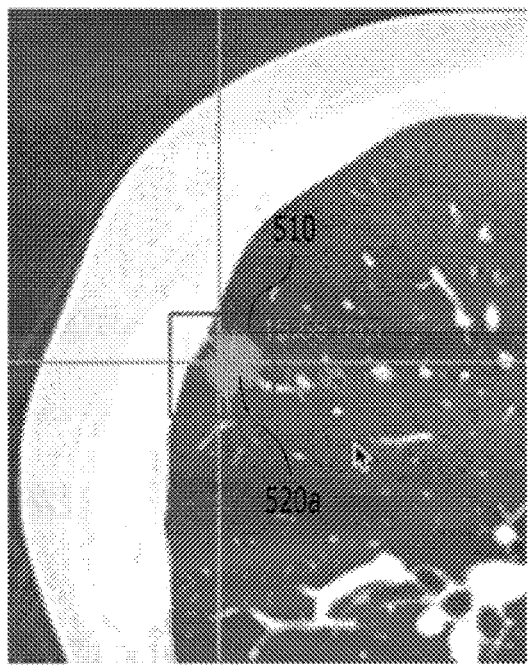
FIGS. 7A and 7B are enlarged views of portion A of FIG. 6, and is a diagram illustrating an example of a user input on the user interface for serial images analysis according to several embodiments of the present disclosure.
Figure 7B:
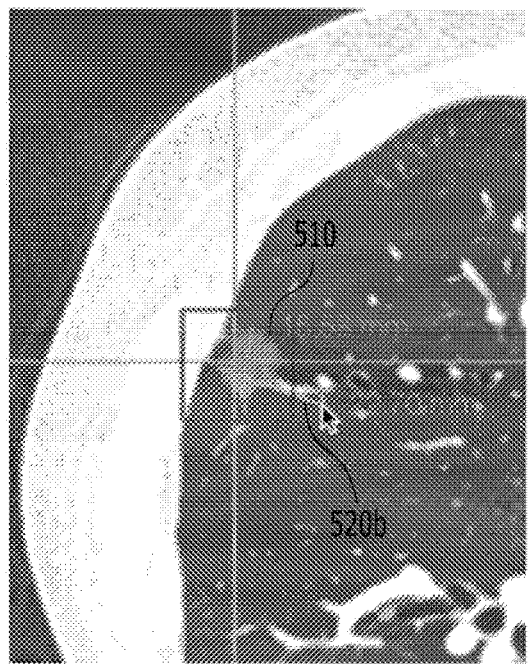

FIGS. 7A and 7B are enlarged views of portion A of FIG. 6, and is a diagram illustrating an example of a user input on the user interface for serial images analysis according to several embodiments of the present disclosure.

Figure 8A:
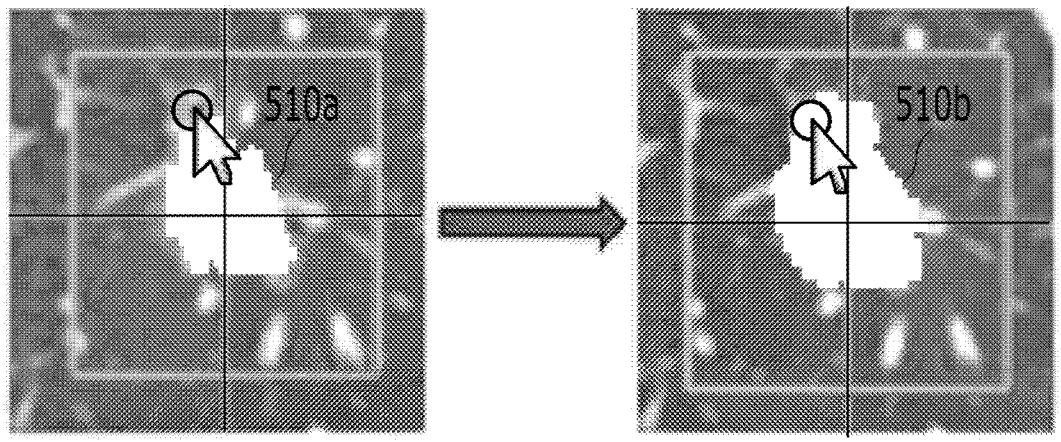
FIGS. 8A and 8B are diagrams illustrating an example of a user input on the user interface for serial images analysis according to several embodiments of the present disclosure.
Figure 8B:
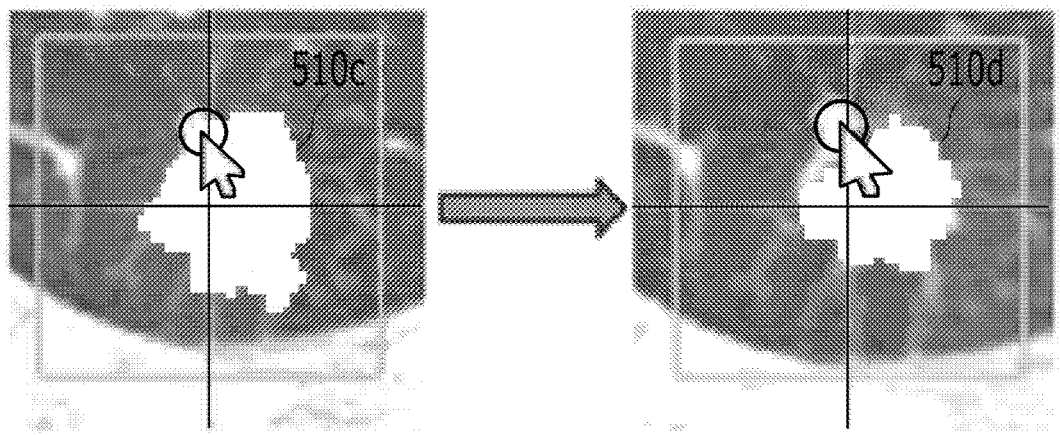

FIGS. 8A and 8B are diagrams illustrating an example of a user input on the user interface for serial images analysis according to several embodiments of the present disclosure.

Referring to FIG. 5, the user interface 200 may display a first cross-sectional image, a second cross-sectional image, and a third cross-sectional image related to a first image on the first area 210 of the user interface (operation S110). The processor 120 may control the output unit 140 so as to display the first cross-sectional image, the second cross-sectional image, and the third cross-sectional image related to the first image on the first area 210.

For example, referring to FIG. 6, in response to a selection of a user for the first image 231a on the third area 230, the first area 210 may display three cross-sectional images 310, 320, and 330 related to the first image 231a.

Referring back to FIG. 5, the user interface 200 may display candidate nodule information related to the first image 231a on at least one of the first cross-sectional image 310, the second cross-sectional image 320, and the third cross-sectional image 330. The processor 120 may control the output unit 140 so as to display the candidate nodule information related to the first image 231a on at least one of the first cross-sectional image 310, the second cross-sectional image 320, and the third cross-sectional image 330.

For example, referring to FIG. 6, in response to the selection of the user for the first image 231a on the third area 230, the first area 210 may display the candidate nodule information A related to the first image 231a while overlapping the three cross-sectional images 310, 320, and 330 related to the first image 231a.

The candidate nodule information A may be generated based on a first nodule data set related to the first image 231a. The first nodule data set may be obtained by the server by inputting the first image 231a to the deep learning algorithm, and include nodule data for a nodule detected from the first image 231a.

FIGS. 6 and 7 illustrate the example in which the candidate nodule information A generated based on location data, segmentation data, and diameter data of the nodule included in the first nodule data set is displayed on the first area 210. More particularly, FIGS. 6 and 7 illustrate the candidate nodule information A including segmentation data 510 and diameter data 520. However, the present disclosure is not limited thereto, and each candidate nodule information may be generated so as to further include volume data, type classification data, Lung-RADS score data, or malignancy risk data for each nodule.

In the meantime, the candidate nodule information A may be displayed on at least one cross-sectional image among the first cross-sectional image 310, the second cross-sectional image 320, and the third cross-sectional image 330 displayed on the first area 210. For example, the candidate nodule information A may be displayed on the cross-sectional image in which each nodule determined based on the diameter data of each nodule is viewed largest. For example, when a C0 nodule has the largest diameter in the cross-sectional image 187 included in the first cross-sectional image, the candidate nodule information A for the C0 nodule may be displayed on the cross-sectional image 187 of the first cross-sectional image. Otherwise, the candidate nodule information A may be displayed on a predetermined cross-sectional image designated by the user. For example, the user may designate that all of the nodule information are displayed only on the first cross-sectional image.

However, the present disclosure is not limited thereto, and when two or more nodule data are included in the candidate nodule information A, each nodule data may be displayed on the cross-sectional image in a different method. Referring to FIG. 6, the diameter data 520 included in the candidate nodule information A may be displayed while overlapping only on the first cross-sectional image 310, and the segmentation data 510 included in the candidate nodule information A may be displayed while overlapping all of the first cross-sectional image 310, the second cross-sectional image 320, and the third cross-sectional image 330.

Referring back to FIG. 5, the candidate nodule information A associated with the user input may be determined as first nodule information related to the first image 231a based on the user input on the user interface 200 (operation S130). The processor 120 may determine the candidate nodule information A associated with the user input as the first nodule information related to the first image 231a based on the user input received through the input unit 150.

The user input may be received through the first area 210 or the second area 220. In particular, the user input may be received through the candidate nodule information A of the first area 210 or the first nodule detailed information 222 of the second area 220.

The user input may include the change input or the confirmation input.

The change input may be the user input for changing at least a part of the candidate nodule information associated with the change input. That is, in the case where the candidate nodule information which is generated from the nodule data set obtained through the deep learning algorithm of the server and displayed as the initial value corresponds to the nodule actually existing in the first image 231a, but the values of some data (for example, the diameter data and the segmentation data) need to be changed, the user may input the change input.

The confirmation input may be the user input for fixing the candidate nodule information associated with the confirmation input. That is, in the case where the candidate nodule information which is generated from the nodule data set obtained through the deep learning algorithm of the server and displayed as the initial value corresponds to the nodule actually existing in the first image 231a and the value of the data does not need to be changed, the user may input the confirmation input.

In the meantime, based on the user input, the candidate nodule information associated with the user input may be determined as the first nodule information related to the first image.

For example, in the case where the user input is the change input, the candidate nodule information associated with the user input may be changed based on the change input, and the changed candidate nodule information may be directly determined as the first nodule information without a separate confirmation input.

Otherwise, when the confirmation input for the changed candidate nodule information is input, the changed candidate nodule information may be determined as the first nodule information. That is, when the confirmation input is input subsequent to the change input, the changed candidate nodule information may be determined as the first nodule information.

Otherwise, when the user input is the confirmation input, the candidate nodule information associated with the user input may be determined as the first nodule information. As described above, when the change input is input before the confirmation input, the changed candidate nodule information may be determined as the first nodule information according to the confirmation input.

Otherwise, when the user input is not input, the candidate nodule information for which the user input is not input may be directly determined as the first nodule information. That is, when both the change input and the confirmation input are not performed for the candidate nodule information, the corresponding candidate nodule information may be directly determined as the first nodule information. However, the present disclosure is not limited thereto, and the user may set the candidate nodule information for which any user input is not input to be determined as not the first nodule information.

Otherwise, the user may also perform an input determining that the candidate nodule information is not the first nodule information. The foregoing examples are merely illustrative, and do not limit the present disclosure.

The user input according to several embodiments of the present disclosure will be described with reference to FIGS. 6 to 8.

In relation to the change input in the first area 210, FIGS. 7A and 7B illustrate an example, in which diameter data 520a included in the candidate nodule information A is displayed in the form of an indicator (see FIG. 7A), and an example in which diameter data 520b included in the candidate nodule information A is changed according to the change input for the indicator (see FIG. 7B). In this case, the change input of the user may be a selection, such as a clock on one end of the indicator, and a drag and drop that extends one end of the selected indicator in a desired length and direction. In this case, the user interface 200 may additionally display a graphic element for intuitively displaying to the user that the one end of the indicator is selectable or has been selected. For example, when a mouse pointer of the user hovers on one end of the indicator, a peripheral portion of the one end of the indicator may be highlighted. However, the present disclosure is not limited thereto, and the change input may be any form of input including, for example, changing the diameter data value itself, which is accompanied by the indicator.

The diameter data 520 of the candidate nodule information A associated with the change input may be changed from 11.95 mm (520a) to 22.70 mm (520b) based on the change input illustrated in FIGS. 7A and 7B. Further, the volume data, the segmentation data, the Lung-RADS score, and/or the malignancy risk data associated with the diameter data may be changed by reflecting the changed diameter data at the same time. For example, when the diameter data of the candidate nodule information A is changed to increase from 11.95 mm to 22.70 mm, the segmentation data may be changed to a mask image enlarged by the changed diameter, and in the meantime, the Lung-RADS score data and the malignancy risk data may also be changed to increase. Further, the candidate nodule information in which the value of the diameter data is changed to 22.70 mm or the candidate nodule information in which the associated data (that is, the volume data, the segmentation data, Lung-RADS score data, and/or the malignancy risk data) is changed together with the value of the diameter data may be determined as the first nodule information related to the first image 231a. Otherwise, the foregoing changed candidate nodule information may be finally determined as the first nodule information related to the first image 231a when the confirmation input is received. The foregoing example is merely the embodiment for expressing the change of the data for the candidate nodule information in response to the change input, and does not limit the present disclosure.

In relation to the change input in the first area 210, FIGS. 8A and 8B illustrate an example in which the segmentation data included in the candidate nodule information A is displayed in the form of the mask image, and the mask image is changed so as to further include an additional area according to the change input for the mask image (see FIG. 8A) or the mask image is changed so as to exclude a part of an existing area (see FIG. 8B). In this case, the change input of the user may be a selection, such as a click, for the partial area of the mask image, and a drag and drop that extends the selected area to an adjacent area or in which the selected area is excluded. In this case, the user interface 200 may additionally display the graphic element for intuitively displaying the area to be extended or excluded according to the change input to the user. For example, it is possible to intuitively display that the partial area of the mask image included in the corresponding circle element is to be extended or excluded by displaying a circular element having a predetermined size based on a mouse pointer of the user.

Based on the change input illustrated in FIGS. 8A and 8B, the value of the segmentation data of the candidate nodule information A associated with the change input may be changed so as to further include the additional area (see FIG. 8A) or may be changed so as to exclude a part of the existing area (see FIG. 8B). Further, the candidate nodule information in which the value of the segmentation data may be determined as the first nodule information related to the first image 231a. Otherwise, the foregoing changed candidate nodule information may be finally determined as the first nodule information related to the first image 231a when the confirmation input is received.

In relation to the change input and/or the confirmation input in the second area 220, the second area 220 illustrated in FIG. 6 may be referred.

The change input in the second area 220 may be a check box selection or a check box selection release in expanded nodule detailed information I. FIG. 6 illustrates the example in which the nodule detailed information 222a consists of the identification data, the segmentation data, the location data, the diameter data, the volume data, and Lung-RADS score data, and the expanded nodule detailed information I consists of the type segmentation data and other characteristic data. One or more characteristic data included in the expanded nodule detailed information I may include data for the detailed characteristic of the nodule, such as whether the corresponding nodule is speculated, and whether the corresponding nodule is calcified.

By the change input in the second area 220, the candidate nodule information associated with the change input may be changed, and the changed candidate nodule information may be determined as the first nodule information related to the first image 231a. For example, when a selection of a solid check box of Nodule Type is released and a GGN check box is selected in the expanded nodule detailed information I of the first nodule detailed information 222a, the value of the type classification data of the candidate nodule information associated with the first nodule detailed information 222a may be changed from solid to GGN, and the changed candidate nodule information may be determined as the first nodule information related to the first image 231a. Otherwise, the foregoing changed candidate nodule information may be finally determined as the first nodule information related to the first image 231a when the confirmation input is received.

In the meantime, the confirmation input in the second area 220 may be a selection for an icon C illustrated at a right end of the nodule detailed information 222a.

By the confirmation input in the second area 220, the candidate nodule information associated with the confirmation input may be determined as the first nodule information related to the first image 231a. For example, by the confirmation input of selecting the check icon (the upper end of C) of the first nodule detailed information 222a, the candidate nodule information associated with the first nodule detailed information 222a may be determined as the first nodule information related to the first image 231a.

Otherwise, when the change input and the confirmation input are sequentially input for the first nodule detailed information 222a of the second area 220, that is, the change input is received through the expanded nodule detailed information I and subsequently, the selection for the icon C is input, the candidate nodule information associated with the first nodule detailed information 222a may be changed based on the change input, and the changed candidate nodule information may be determined as the first nodule information related to the first image 231a based on the confirmation input.

By determining the candidate nodule information as the first nodule information based on the user input on the user interface, it is possible to intuitively and simply perform work. That is, the user is capable of directly performing the user input on the nodule information of interest, and the candidate nodule information may be determined as the first nodule information based on the user input, so that the review of the nodule data obtained through the deep learning algorithm may be intuitively and simply performed. Further, it is possible to improve accuracy of image reading.

In the meantime, the determined first nodule information or the first nodule detailed information may be reflected to the first nodule data set and generate a second nodule data set. The processor 120 may generate the second nodule data set by reflecting the first nodule information or the first nodule detailed information to the first nodule data set. For example, when some of the candidate nodule information generated based on the first nodule data set is changed based on the change input and then is determined as the first nodule information, and the remaining candidate nodule information is determined as the first nodule information based on the confirmation input, the processor 120 may newly generate the second nodule data set by reflecting the content of the changed candidate nodule information to the first nodule data set. That is, separate from the first nodule data set obtained by inputting the image to the deep learning algorithm, the second nodule data set to which the user input is reflected may be newly generated.

The generated second nodule data set may be transmitted to the server. The processor 120 may control the network unit 110 so as to generate the second nodule data set and transmit the generated second nodule data set to the server. After the second nodule data set is generated, the generated second nodule data set may be automatically transmitted to the server immediately or when satisfying a predetermined condition (when a predetermined time elapses after the second nodule data set is generated). Otherwise, the second nodule data set may be transmitted to the server in response to the input of the user desiring to transmit the second nodule data set to the server.

Alternatively, instead of directly generating the second nodule data set, the processor 120 may make the second nodule data set may be generated in the server by transmitting the first nodule information or the first nodule detailed information to the server. That is, by transmitting the first nodule information or the first nodule detailed information determined based on the user input to the server, the processor of the server may directly generate the second nodule data set by reflecting the first nodule information or the first nodule detailed information to the first nodule data set.

Referring back to FIG. 5, the first nodule information may be displayed in the method in which the candidate nodule information associated with the user input is replaced with the first nodule information (operation S140). The processor 120 may control the output unit 140 so as to display the first nodule information by the method of replacing the candidate nodule information with the first nodule information.

For example, when the change input is input on the user interface, the candidate nodule information associated with the change input may be changed based on the change input, and the candidate nodule information (that is, the candidate nodule information before the change) that has been displayed before may be replaced with the first nodule information (that is, the changed candidate nodule information) and displayed. However, the present disclosure is not limited thereto, and the first nodule information may be shown together with the candidate nodule information. For example, the candidate nodule information (that is, the candidate nodule information before the changed) that has been displayed before and the first nodule information (that is, the changed candidate nodule information) may be displayed while overlapping or may be disposed side by side so as not to overlap and displayed.

Otherwise, when the confirmation input is input on the user interface, the candidate nodule information that has been displayed before may be replaced with the first nodule information determined according to the confirmation input and displayed. When the confirmation input is directly input without the change input for the candidate nodule information, the candidate nodule information may be directly determined as the first nodule information without being changed, so that the replacement of the candidate nodule information with the first nodule information may not be visually recognized to the user. However, the present disclosure is not limited thereto, for example, when the confirmation input is directly input without the change input for the candidate nodule information, the candidate nodule information may be continuously displayed without replacing the candidate nodule information with the first nodule information.

Figure 9A:
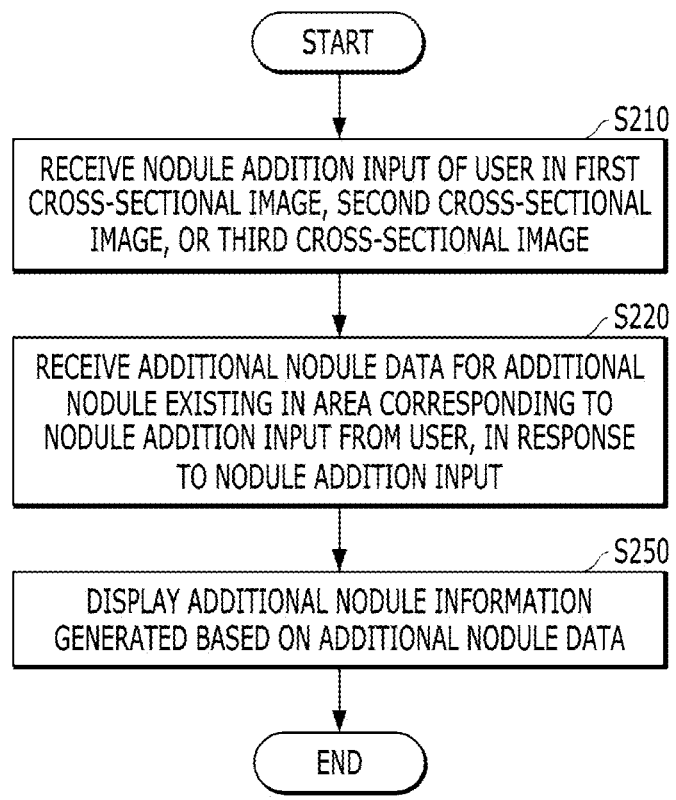
FIG. 9A is a flowchart for processing a nodule additional input according to several embodiments of the present disclosure.

FIGS. 9A and 9B are flowcharts illustrating processing a nodule addition input according to several embodiments of the present disclosure.

The nodule addition input may be a user input for adding a nodule that is not detected through the deep learning algorithm, but is read as existing in the image.

The user interface 200 may allow the nodule addition input of the user on the first cross-sectional image 310, the second cross-sectional image 320, or the third cross-sectional image 330 of the first area 210. The processor 120 may receive the nodule addition input of the user through the input unit 150 (operation S210).

The nodule addition input may be performed by a drag and drop operation or an operation of clicking one or more points on the first cross-sectional image 310, the second cross-sectional image 320, or the third cross-sectional image 330. Otherwise, the nodule addition input may be performed by a click operation for "Add Nodule" button on the user interface 200. Otherwise, the nodule addition input may be performed by a combination of the click operation for "Add Nodule" button and the drag and drop operation or an operation of clicking one or more points on the first cross-sectional image 310, the second cross-sectional image 320, or the third cross-sectional image 330.

In the meantime, in response to the nodule addition input, additional nodule data for the additional nodule existing in the area corresponding to the nodule addition input may be obtained (operations S220 to S240).

The additional nodule data may include identification data, location data, segmentation data, diameter data, volume data, type classification data, Lung-RADS score data, and malignancy risk data for the additional nodule existing in the area corresponding to the nodule addition input.

In relation to a method of obtaining the additional nodule data, FIG. 9A illustrates an example of a method of obtaining additional nodule data by receiving additional nodule data from the user, and in the meantime, FIG. 9B illustrates an example of a method of obtaining additional nodule data through a calculation performed through the deep learning algorithm in the server. However, the present disclosure is not limited thereto, and for example, the method of receiving additional nodule data from the user and the method of obtaining additional nodule data through the computation in the server may be combined and used. Otherwise, a method of obtaining additional nodule data based on a predetermined condition may be selected. For example, only any one method arbitrarily designated by the user may be used, or any one method may be automatically used based on whether a nodule is detected in the area corresponding to the additional nodule data.

First, referring to FIG. 9A, in response to the nodule addition input, the additional nodule data for the additional nodule existing in the area corresponding to the nodule addition input may be received from the user. For example, values of identification data, location data, segmentation data, diameter data, volume data, type classification data, Lung-RADS score data, and malignancy risk data for the additional nodule data may be received from the user.

Otherwise, a value for at least some data of the additional nodule data may be received from the user, and remaining data of the additional nodule data may be calculated based on the received data.

For example, coordinate (x1, y1) and coordinate (x2, y2) on the cross-sectional image may be received from the user, and a distance (for example, $\sqrt{(x_2^2-x_1^2)+(y_2^2-y_1^2)}$) between the coordinate (x1, y1) and the coordinate (x2, y2) may be calculated as diameter data of the additional nodule based on the received coordinates. However, the present disclosure is not limited thereto, and a three-dimensional input may be received from the user, and a distance (for example, $\sqrt{(x_2^2-x_1^2)+(y_2^2-y_1^2)+(z_2^2-z_1^2)}$) between coordinate (x1, y1, z1) and coordinate (x2, y2, z3) may be calculated as diameter data of the additional nodule based on the received coordinates. Otherwise, the additional nodule data including the calculated values may be generated by receiving the value of the diameter data of the additional nodule from the user, and calculating values of volume data and Lung-RADS score data of the additional nodule data based on the received value of the diameter data. However, the present disclosure is not limited thereto.

Alternatively, referring to FIG. 9B, in response to the nodule addition input, the calculation for the nodule addition input may be requested to the server (S230). The processor 120 may control the network unit 110 so as to request the calculation for the nodule addition input from the server in response to the nodule addition input received through the input unit 150.

In this case, the calculation performed in the server may be the obtainment of the additional nodule data that is the data for the additional nodule existing in the area corresponding to the nodule addition input by inputting the area corresponding to the nodule addition input to the deep learning algorithm.

In the calculation, whether the nodule is detected in the area on the first area 210 corresponding to the nodule addition input may be first determined based on the deep learning algorithm. For example, whether the additional nodule is detected in the area on the first area 210 corresponding to the nodule addition input may be first determined based on the nodule detection module.

When the nodule is detected, the additional nodule data may be generated based on the deep learning algorithm. For example, based on the location data of the additional nodule obtained from the nodule detection module, segmentation data of the additional nodule may be obtained through the nodule measurement nodule. Otherwise, based on the location data and the segmentation data of the additional nodule, diameter data and volume data of the additional nodule may be obtained. Otherwise, based on the location data and the segmentation data of the additional nodule, type classification data of the additional nodule may be obtained through the nodule type classification module. Otherwise, based on the diameter data, the volume data, and the type classification data of the additional nodule, Lung-RADS score data and/or malignancy risk data of the additional nodule may be obtained.

In the meantime, the additional nodule information generated based on the additional nodule data may be displayed on the user interface 200 (S250).

The user interface 200 may display the additional nodule information generated based on the additional nodule data on at least one of the first cross-sectional image 310, the second cross-sectional image 320, and the third cross-sectional image 330 displayed in the first area 210. For example, the additional nodule information determined based on the diameter data of the additional nodule data may be displayed on the cross-sectional image in which the additional nodule is viewed largest. The foregoing description merely represents one embodiment in which the additional nodule information generated based on the additional nodule data is displayed, and a predetermined display method by which the additional nodule information is most intuitively visible to the user may also be included in the present disclosure.

The user interface 200 may display additional nodule detailed information generated so as to be associated with the additional nodule information based on the additional nodule data on the second area 220.

As described above, by allowing the nodule addition input of the user on the image, the user is capable of directly performing the nodule addition input on the nodule to be added and thus it is possible to intuitively and simply perform work. Further, by generating the additional nodule data based on the deep learning algorithm or the nodule addition input of the user, the user may reduce inconvenience of having to manually input data for the nodule desired to be added. Further, the user is capable of adding the nodule data omitted in the nodule data set obtained through the deep learning algorithm, thereby improving accuracy of image reading.

Figure 10:
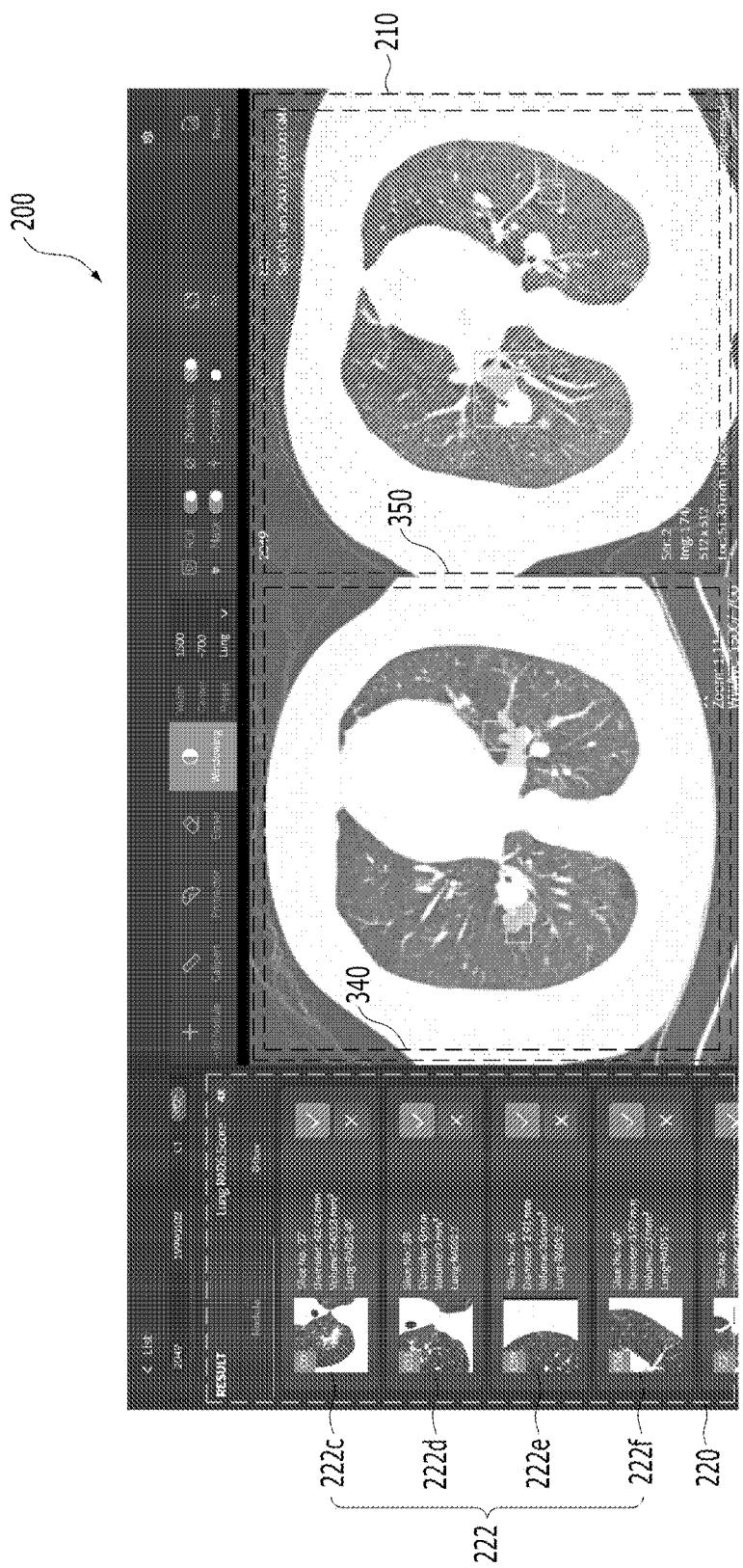
FIG. 10 is a diagram illustrating an example of the user interface for serial images analysis according to several embodiments of the present disclosure.

FIG. 10 is a diagram illustrating an example of the user interface for serial images analysis according to several embodiments of the present disclosure.

Referring to FIG. 10, the fourth area 240 may be displayed so as to include the list 241 of the related images of the first image 231a in response to the selection for the first image 231a. The related image may be the image photographed at a different time from that of the first image 231a for the same object to be photographed as that of the first image 231a. More particularly, the related image may be the image photographed before the photographing time of the first image 231a for the same object to be photographed as that of the first image 231a.

In the meantime, in response to the comparative selection input of the user for selecting the second image 241a on the displayed fourth area 240, the first cross-sectional image for comparison 340 related to the first image 231a and the second cross-sectional image for comparison 350 related to the second image 241a may be displayed in the first area 210.

The first cross-sectional image for comparison 340 and the second cross-sectional image for comparison 350 may be one of the first cross-sectional image, the second cross-sectional image, or the third cross-sectional image. For example, when the first cross-sectional image for comparison 340 is the axial view image (the first cross-sectional image) of the first image 231a, the second cross-sectional image for comparison 350 may be the axial view image (the first cross-sectional image) of the second image 241a. Otherwise, when the first cross-sectional image for comparison 340 is the coronal view image (the second cross-sectional image) of the first image 231a, the second cross-sectional image for comparison 350 may be the coronal view image (the second cross-sectional image) of the second image 241a. Otherwise, when the first cross-sectional image for comparison 340 is the sagittal view image (the third cross-sectional image) of the first image 231a, the second cross-sectional image for comparison 350 may be the sagittal view image (the third cross-sectional image) of the second image 241a. However, the present disclosure is not limited thereto, and the first cross-sectional image for comparison 340 and the second cross-sectional image for comparison 350 may also be designated as a cross-sectional image in a predetermined direction by the user.

In the meantime, and the first cross-sectional image for comparison 340 and the second cross-sectional image for comparison 350 may be displayed while interlinking with each other. For example, when and the first cross-sectional image for comparison 340 is zoomed in or zoomed out in a predetermined ratio according to a user input, the second cross-sectional image for comparison 350 may also be zoomed in or zoomed out in a corresponding ratio.

Otherwise, when a point having a predetermined coordinate on the second cross-sectional image for comparison 350 is highlighted according to a user input, a point of a corresponding coordinate of the first cross-sectional image for comparison 340 may be highlighted.

Otherwise, in response to the selection of the predetermined nodule detailed information on the second area 220, the first cross-sectional image for comparison 340 and the second cross-sectional image for comparison 350 corresponding to the selected nodule detailed information may be displayed. For example, when the user selects the nodule detailed information 222a on the second area 220, an area corresponding to the selected nodule detailed information 222a may be displayed at the center of each cross-sectional image for comparison (that is, the first cross-sectional image for comparison and the second cross-sectional image for comparison), or an area corresponding to the selected nodule detailed information 222a may be displayed may be zoomed in and displayed in each cross-sectional image for comparison.

In the meantime, when the first cross-sectional image for comparison 340 and the second cross-sectional image for comparison 350 are displayed in response to the comparative selection input, the second nodule information generated based on the third nodule data set may be additionally displayed on the first cross-sectional image for comparison 340. Further, the second nodule detailed information generated so as to be associated with the second nodule information based on the third nodule data set may be additionally displayed on the second area 220.

The third nodule data set may be obtained by matching the first image 231a and the second image 241a through the deep learning algorithm in the server in order to identify the change of the nodule existing in the first image 231a through the comparison with the second image 241a.

The matching of the first image 231a and the second image 241a may include an operation of matching a relative location relationship between two photographed images according to a difference in a photographing time or a difference of a photographing subject. For example, the first image 231a and the second image 241a may be matched by comparing a feature point, brightness, and the like in each image, and based on the matching, it is possible to identify an aspect in which a predetermined nodule existing in the first image 231a is changed compared to the second image 241a.

In comparison with the first nodule data set described above, the third nodule data set may be compared with the first nodule data set including the data of the nodule itself detected in the first image 231a in that the third nodule data set includes data on a change aspect of the nodule detected in the first image 231a, that is, the nodule change aspect identified through the comparison between the first image 231a and the second image 241a.

For example, according to Lung-RADS Version 1.1, the value of Lung-RADS score data of a solid type nodule (hereinafter, a "first nodule") having a diameter less than 6 mm detected in the first image 231a may be 2, and the malignancy risk data thereof may be <1%. That is, the first nodule data set for the first image 231a may include nodule data, such as {diameter data=6 mm; type classification data=Solid; Lung-RADS score data=2; malignancy risk data=<1%}, for the detected first nodule.

However, when the first image 231a is compared with the second image 241a, when the first nodule is detected only in the first image 231a, that is, the first nodule does not exist at the photographing time of the second image 241a, but is identified as a newly generated nodule, the value of the Lung-RADS score data of the first nodule may increase to 3, and the malignancy risk data may also increase to 1 to 2%. That is, the third nodule data set for the first image 231a may include nodule data, such as {diameter data=6 mm; type classification data=Solid; Lung-RADS score data=3; malignancy risk data=1 to 2%}, for the detected first nodule.

When the first image 231a is compared with the second image 241a, various change aspects may be identified, such as the first nodule may be identified to be grown, the first nodule may be identified as maintained at a constant size, or the first nodule is identified to be decreased. The foregoing example is merely the embodiment, and does not limit the present disclosure.

In the meantime, the third nodule data set may be received from the server and updated so that the first nodule information is reflected, and the second nodule information may be generated based on the updated third nodule data set.

For example, the first candidate nodule information corresponding to the first nodule may be changed based on the user input on the user interface, and may be determined as the first nodule information. For example, the diameter data of the first candidate nodule information is 6 mm, but the diameter data of the first candidate nodule information is changed to 7 mm based on the user input that is the change input, and the first candidate nodule information in which the diameter data is changed to 7 mm may be determined as the first nodule information. When the third nodule data set is updated by reflecting the first nodule information, the third nodule data set may be updated so as to include the nodule data, such as {diameter data=7 mm; type classification data=Solid; Lung-RADS score data=4A; malignancy risk data=5 to 15%}, for the first nodule.

The second nodule information may be generated based on the updated third nodule data set. That is, according to the foregoing example, the second nodule information may be generated at least partially based on {diameter data=7 mm; type classification data=Solid; Lung-RADS score data=4A; malignancy risk data=5 to 15%}. The foregoing example is merely the embodiment, and does not limit the present disclosure. For example, when the change input for the first candidate nodule information is not received, the second nodule information may be generated based on the value of the nodule data of the third nodule data set, that is, at least partially based on {diameter data=6 mm; type classification data=Solid; Lung-RADS score data=3; malignancy risk data=1-2%}.

The generated second nodule information may be displayed on the first cross-sectional image for comparison. For example, the first nodule information related to the first image 231a may be displayed in the first cross-sectional image for comparison related to the first image 231a, and at least a part of the second nodule information may be additionally displayed. For example, at least a part of the second nodule information may be displayed while overlapping the first nodule information, or may be disposed with the first nodule information side by side so as not to overlap the first nodule information and displayed. In this case, the second nodule information may be displayed so as to be visually discriminated from the first nodule information. Otherwise, the second nodule information may be displayed in the first cross-sectional image for comparison by the method of replacing the first nodule information displayed in the first cross-sectional image for comparison with the second nodule information. Otherwise, only the second nodule information may be displayed in the first cross-sectional image for comparison.

In the meantime, the second nodule detailed information associated with the second nodule information may be generated based on the updated third nodule data set. The generated second nodule detailed information may be displayed on the second area 220. For example, the first nodule detailed information related to the first image 231a may be displayed on the second area 220, and at least a part of the second nodule detailed information may be additionally displayed. For example, at least a part of the second nodule detailed information may be displayed while overlapping the first nodule detailed information, or may be disposed with the first nodule detailed information side by side so as not to overlap the first nodule detailed information and displayed. In this case, the second nodule detailed information may be displayed so as to be visually discriminated from the first nodule detailed information.

For example, when the Lung-RADS score data for the C0 nodule of the third nodule data set is updated from 3 to 4A, the second area 220 may display "Lung-RADS: 4A" in the node detailed information 222a corresponding to the C0 nodule. That is, the first nodule detailed information (herein, Lung-RADS: 3) and the second nodule detailed information (herein, Lung-RADS: 4A) are displayed side by side, and the second nodule detailed information may be visually discriminated from the first nodule detailed information by displaying the first nodule detailed information together with a cancel line. However, the present disclosure is not limited thereto, and the second nodule detailed information may be visually discriminated from the first nodule detailed information, for example, by using a symbol, such has an arrow, by inserting an assistant highlighted figure, or changing a text form (thickness, inclination, underline, font, and color).

As described above, it is possible to intuitively read a progress of each nodule by displaying the first image 231a and the second image 241a that is the related image together and particularly, displaying the first image 231a and the second image 241a by interlocking both images. Further, the second nodule information and the second nodule detailed information to which the change aspect of the nodule is reflected are automatically generated and displayed on the user interface 200, so that the user may reduce inconvenience of having to compare the first image 231a and the second image 241a one by one with naked eyes and updating the first nodule information and/or the first nodule detailed information to the second nodule information and/or the second nodule detailed information. Further, particularly, it is possible to increase accuracy of the Lung-RADS score data, it is possible to improve accuracy of the image reading and apply a more appropriate management method.

Figure 11:
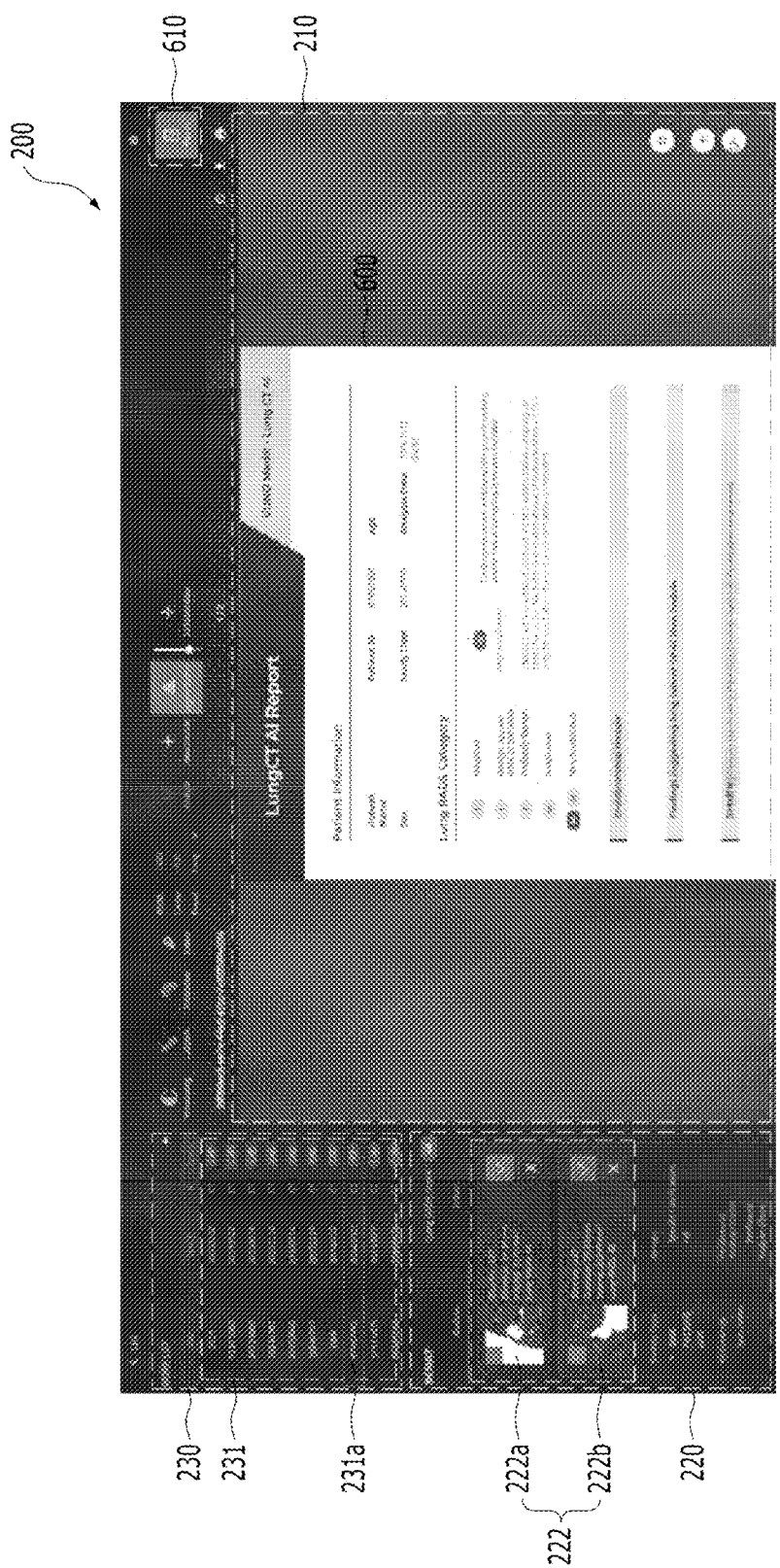
FIG. 11 is a diagram illustrating an example of a method of displaying a report according to several embodiments of the present disclosure.

FIG. 11 is a diagram illustrating an example of a method of displaying a report according to several embodiments of the present disclosure.

Referring to FIG. 11, in response to a report request input of the user, a report related to the first image 231a may be generated.

The report request input of the user may be, for example, a click on a "Report" button 610. In response to the report request input of the user, the user interface 200 may display the generated report 600 on the first area 210.

When the second nodule information exists, the report may be generated based on the second nodule information.

For example, when the second image 241a that is the related image of the first image 231a exists, the third nodule data set may be obtained from the server based on the first image 231a and the second image 241a, and the second nodule information to be displayed on the user interface 200 may have been generated based on the obtained third nodule data set and existed.

That is, when the second image 241a that is the related image of the first image 231a exists, a process of generating the second nodule information to which the nodule change aspect is reflected according to the comparative selection input of the user for the second image 241a is required, and thus, the report for the first image 231a may be generated based on the generated second nodule information.

According to the demand of the process of generating the second nodule information, it is possible to assist the user not to omit the procedure of comparing the first image 231a with the related image (that is, the second image 241a) (that is, the procedure of selecting the second image 241a from the list 241 of the related images, and interlocking and displaying the first cross-sectional image for comparison 340 and the second cross-sectional image for comparison 350 together on the first area 220), so that the user is capable of generating a report including more accurate the Lung-RADS score data.

Otherwise, when the second nodule information does not exist, the report may be generated based on the first nodule information.

For example, when the related image of the first image 231*a* does not exist, that is, the first image 231*a* is the image first photographed for the object to be photographed, the first nodule data set may be obtained from the server based on the first image 231*a*, and the first nodule information to be displayed on the user interface 200 is generated based on the obtained first nodule data set. However, the second nodule information to which the nodule change aspect is reflected through the comparison between the first image 231*a* and the second image 241*a* cannot be generated.

That is, when the second image 241*a* that is the related image of the first image 231*a* does not exist, the user may generate the report for the first image 231*a* based on the first nodule information about the nodule detected from the first image 231*a* without performing the process of comparing the first image 231*a* with the related image.

In the meantime, when the report is generated, the user may select an item to be included in the report. For example, the user may set the report to be generated while including a data item, that is, at least a part of the location data, the segmentation data, the diameter data, the volume data, the type classification data, the Lung-RADS score data, and the malignancy risk data, includable in the first nodule information or the second nodule information.

In addition, the report may further include identification information about the object to be photographed, identification information of the user generating the report (for example, identification information of a hospital, identification information of an image reader or a medical staff), and the like.

In the meantime, the report 600 displayed in the first area 210 may be downloaded to or stored in the computing device 100.

Figure 12:
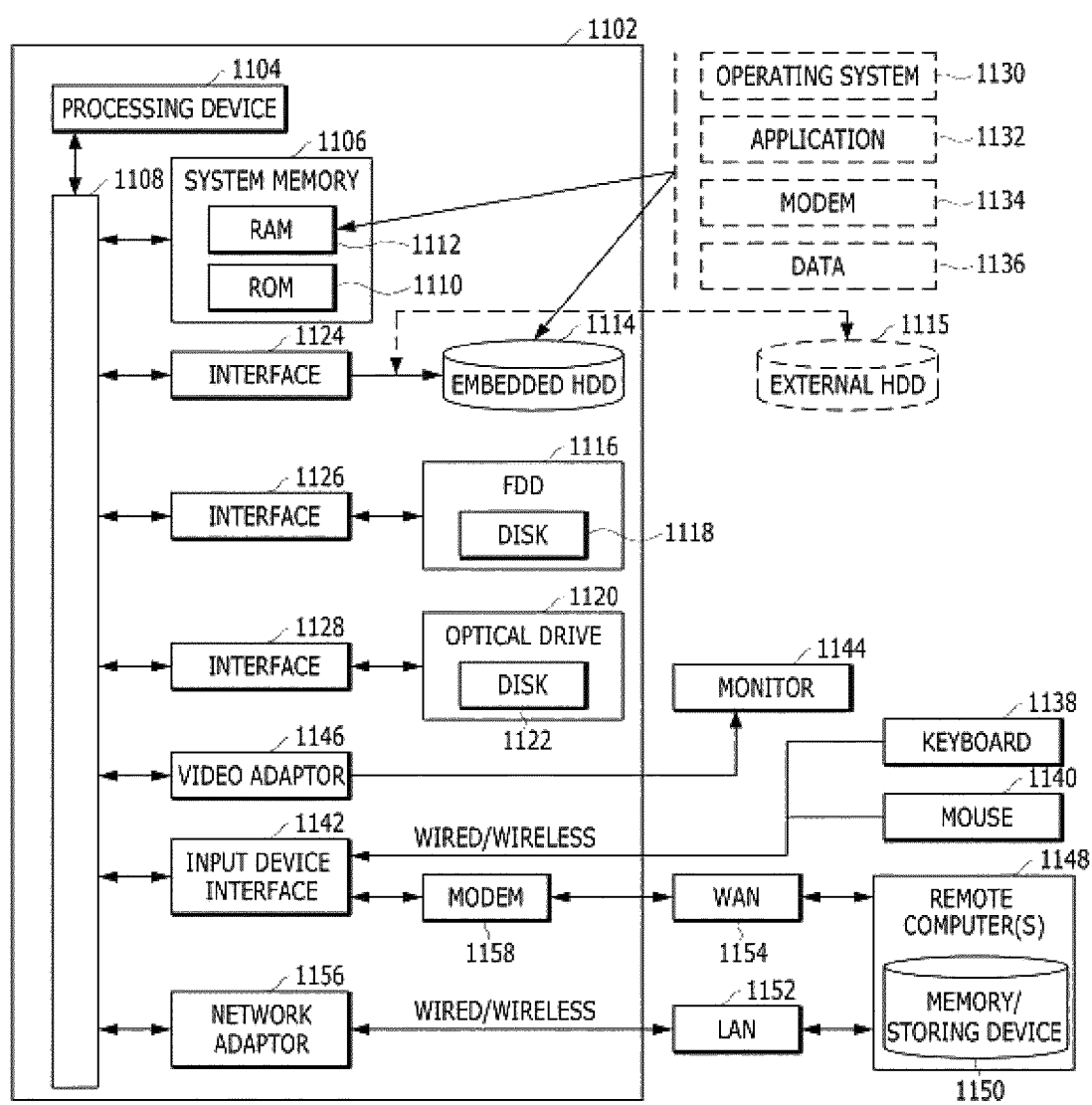
FIG. 12 is a simple and general schematic diagram illustrating an example of a computing environment in which several embodiments of the present disclosure are implementable.

FIG. 12 is a simple and normal schematic view of an computing environment in which the embodiments of the present disclosure may be implemented.

It is described above that the present disclosure may be generally implemented by the computing device, but those skilled in the art will well know that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The embodiments described in the present disclosure may also be implemented in a distributed computing environment in which predetermined tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, temporary and non-temporary media, and movable and non-movable media implemented by a predetermined method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined other media which may be accessed by the computer or may be used to store desired information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal acquired by configuring or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting. The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an operating environment and further, the predetermined media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer(s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is and other means configuring a communication link among computers may be used.

The computer 1102 performs an operation of communicating with predetermined wireless devices or entities which are disposed and operated by the wireless communication, for example, the printer, a scanner, a desktop and/or a portable computer, a portable data assistant (PDA), a communication satellite, predetermined equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined technologies and techniques. For example, data, instructions, commands, information, signals, bits, symbols, and chips which may be referred in the above description may be expressed by voltages, currents, electromagnetic waves, magnetic fields or particles, optical fields or particles, or predetermined combinations thereof.

It may be appreciated by those skilled in the art that various logical blocks, modules, processors, means, circuits, and algorithm steps described in association with the embodiments disclosed herein may be implemented by electronic hardware, various types of programs or design codes (for easy description, herein, designated as software), or a combination of all of them. In order to clearly describe the intercompatibility of the hardware and the software, various components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various embodiments presented herein may be implemented as manufactured articles using a method, an apparatus, or a standard programming and/or engineering technique. The term manufactured article includes a computer program, a carrier, or a medium which is accessible by a predetermined computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of providing a user interface for serial images analysis in a user equipment, comprising:
    displaying a first cross-sectional image, a second cross-sectional image, and a third cross-sectional image on a first area of the user interface, which are related to a first image;
    displaying candidate nodule information related to the first image on at least one of the first cross-sectional image, the second cross-sectional image, and the third cross-sectional image;
    determining the candidate nodule information related to a user input as first nodule information related to the first image, based on the user input on the user interface; and
    displaying the first nodule information in such a way that the candidate nodule information related to the user input is replaced with the first nodule information,
    wherein the candidate nodule information is generated based on a first nodule dataset obtained by inputting the first image to a deep learning algorithm in a server,
    wherein the user input includes a change input for changing a value of diameter data or a value of segmentation data of the candidate nodule information.

2. The method of claim 1, wherein the user input further includes a confirmation input for determining the changed candidate nodule information as the first nodule information,
    wherein the determining the candidate nodule information related to the user input as the first nodule information related to the first image comprising:
    when the user input further includes the confirmation input, determining the changed candidate nodule information as the first nodule information.

3. The method of claim 1, further comprising:
    displaying first nodule detailed information which is generated to be associated with the candidate nodule information or the first nodule information based on the first nodule dataset, on a second area of the user interface,
    wherein the second area on which the first nodule detailed information is displayed is capable of receiving the user input.

4. The method of claim 3, further comprising:
    generating a second nodule dataset by reflecting the first nodule information or the first nodule detailed information to the first nodule dataset,
    wherein the generated second nodule dataset is capable of being transmitted to the server.

5. The method of claim 3, wherein the method further comprising:
    displaying a list of a related image related to the first image on a fourth area of the user interface, in response to a selection input for the first image,
    wherein the related image is an image taken for the same subject as the subject of the first image, at a time before taking the first image.

6. The method of claim 5, further comprising:
    displaying a first cross-sectional image for comparison related to the first image and a second cross-sectional image for comparison related to the second image on the first area, in response to the comparison selection input of a user for the second image among the related images.

7. The method of claim 6, wherein the first cross-sectional image for comparison and the second cross-sectional image for comparison are displayed by interworking.

8. The method of claim 6, further comprising:
    additionally displaying second nodule information generated based on a third nodule dataset on the first cross-sectional image for comparison,
    wherein the third nodule dataset is obtained by matching the first image and the second image through the deep learning algorithm, in order to identify a change of a nodule present in the first image,
    wherein the second nodule information is generated based on the third nodule dataset updated by reflecting the determined first nodule information.

9. The method of claim 8, further comprising:
additionally displaying second nodule detailed information generated to be associated with the second nodule information based on the updated third nodule dataset, on the second area,
wherein the second nodule detailed information is visually distinguished from the first nodule detailed information.

10. The method of claim 8, further comprising:
receiving a report request input for the first image; and
when the second nodule information does not exist, generating a report based on the first nodule information.

11. The method of claim 8, further comprising:
receiving a report request input for the first image; and
when the second nodule information exists, generating a report based on the second nodule information.

12. The method of claim 1, wherein the first nodule dataset includes one or more nodule data, and
the one or more nodule data include at least one of an identification data for the nodule, a location data for the nodule, a segmentation data for the nodule, diameter data for the nodule, a volume data for the nodule, a classification data for the nodule, a Lung-RADS score data for the nodule, or a malignancy risk data for the nodule.

13. The method of claim 12, wherein the displaying the candidate nodule information related to the first image on at least one of the first cross-sectional image, the second cross-sectional image, and the third cross-sectional image comprising:
displaying the candidate nodule information on a cross-sectional image having the largest diameter of the nodule among the first cross-sectional image, the second cross-sectional image, or the third cross-sectional image, based at least on the diameter data.

14. The method of claim 1, further comprising:
receiving an additional nodule data for an additional nodule existing in an area corresponding to a nodule addition input, in response to the nodule addition input of a user in the first cross-sectional image, the second cross-sectional image, or the third cross-sectional image; and
displaying additional nodule information generated based on the additional nodule data.

15. The method of claim 14, wherein the displaying the additional nodule information generated based on the additional nodule data comprising:
additionally displaying the additional nodule information generated based on the additional nodule data on at least one of the first cross-sectional image, the second cross-sectional image, or the third cross-sectional image, and displaying additional nodule detailed information generated to be associated with the additional nodule information based on the additional nodule data, on the second area of the user interface.

16. The method of claim 1, further comprising:
requesting an operation for a nodule addition input to the server, in response to the nodule addition input of a user in the first cross-sectional image, the second cross-sectional image, or the third cross-sectional image; and
receiving an additional nodule data obtained by the operation from the server, and displaying additional nodule information generated based on the received additional nodule data,
wherein the operation is to obtain the additional nodule data, which is data for an additional nodule existing in an area corresponding to the nodule addition input, by inputting the area corresponding to the nodule addition input to the deep learning algorithm, in the server.

17. The method of claim 16, wherein the displaying the additional nodule information generated based on the received additional nodule data comprising:
additionally displaying the additional nodule information generated based on the additional nodule data on at least one of the first cross-sectional image, the second cross-sectional image, or the third cross-sectional image, and displaying additional nodule detailed information generated to be associated with the additional nodule information based on the additional nodule data, on the second area of the user interface.

18. The method of claim 1, further comprising:
displaying an image list including the first image on a third area of the user interface.

19. A device for providing a user interface for serial images analysis, comprising:
a display; and
a processor operatively coupled to the display, the processor configured to:
display to the display a first cross-sectional image, a second cross-sectional image, and a third cross-sectional image on a first area of the user interface, which are related to a first image;
display to the display candidate nodule information related to the first image on at least one of the first cross-sectional image, the second cross-sectional image, and the third cross-sectional image;
determine the candidate nodule information related to a user input as first nodule information related to the first image, based on the user input on the user interface; and
display to the display the first nodule information in such a way that the candidate nodule information related to the user input is replaced with the first nodule information,
wherein the candidate nodule information is generated based on a first nodule dataset obtained by inputting the first image to a deep learning algorithm in the processor,
wherein the user input includes a change input for changing a value of diameter data or a value of segmentation data of the candidate nodule information.

20. The device of claim 19, wherein the user input further includes a confirmation input for determining the changed candidate nodule information as the first nodule information,
wherein determining the candidate nodule information related to the user input as the first nodule information related to the first image comprises:
when the user input further includes the confirmation input, determining the changed candidate nodule information as the first nodule information.

* * * * *